United States Patent
Qian et al.

(10) Patent No.: US 10,137,208 B2
(45) Date of Patent: Nov. 27, 2018

(54) VIVO TUMOR TARGETING AND SPECTROSCOPIC DETECTION WITH SURFACE-ENHANCED RAMAN NANOPARTICLE TAGS

(71) Applicant: EMORY UNIVESITY, Atlanta, GA (US)

(72) Inventors: Ximei Qian, Atlanta, GA (US); Dominic Ansari, Chicago, IL (US); Shuming Nie, Atlanta, GA (US)

(73) Assignee: Emory University, Atlanta, GA (US)

( * ) Notice: Subject to any disclaimer, the term of this patent is extended or adjusted under 35 U.S.C. 154(b) by 1069 days.

(21) Appl. No.: 13/680,524

(22) Filed: Nov. 19, 2012

(65) Prior Publication Data

US 2013/0149247 A1 Jun. 13, 2013

Related U.S. Application Data

(63) Continuation of application No. 12/593,359, filed as application No. PCT/US2008/059117 on Apr. 2, 2008, now abandoned.

(60) Provisional application No. 60/909,656, filed on Apr. 2, 2007.

(51) Int. Cl.
| | | |
|---|---|---|
| A61K 51/00 | (2006.01) | |
| A61K 49/00 | (2006.01) | |
| G01N 21/65 | (2006.01) | |
| A61B 5/00 | (2006.01) | |
| B82Y 5/00 | (2011.01) | |

(52) U.S. Cl.
CPC ...... *A61K 49/0089* (2013.01); *A61K 49/0023* (2013.01); *A61K 49/0032* (2013.01); *A61K 49/0041* (2013.01); *A61K 49/0065* (2013.01); *A61K 49/0093* (2013.01); *G01N 21/658* (2013.01); *A61B 5/0059* (2013.01); *A61B 5/416* (2013.01); *A61B 2503/40* (2013.01); *B82Y 5/00* (2013.01); *Y10S 977/773* (2013.01); *Y10S 977/81* (2013.01)

(58) Field of Classification Search
CPC ............. A61K 49/00; A61K 49/0023; A61K 49/0032; A61K 49/0041; A61K 49/0065; A61K 49/0093; A61K 49/0089; A61B 5/0059; A61B 5/416; A61B 2503/40; G01N 21/658; B82Y 5/00; Y10S 977/773; Y10S 977/81
USPC ............................................................. 494/9.1
See application file for complete search history.

(56) References Cited

U.S. PATENT DOCUMENTS 5,866,336 A 2/1999 Nazarenko et al.
2004/0023415 A1* 2/2004 Sokolov et al. ............. 436/518
2005/0136258 A1 6/2005 Nie
2005/0191665 A1 9/2005 Su et al.
2006/0054506 A1 3/2006 Natan
2006/0073336 A1 4/2006 Zhang et al.
2006/0234248 A1 10/2006 Sun et al.

FOREIGN PATENT DOCUMENTS

WO 2005030996 4/2005
WO 2005/062741 A1 7/2005
WO 2007/032653 A1 4/2006

OTHER PUBLICATIONS

Doering et al., (2003), "Spectroscopic Tags Using Dye-Embedded Nanoparticles and Surface-Enhanced Raman Scattering.", Analytical Chemistry, 75(22): 6171-6176.
Hong et al., (2006), "In situ observation of place exchange reactions of gold nanoparticles. Correlation of monolayer structure and stability.", Chem Commun, (Camb)(22): 2347-2349.
Hostetler et al., (1999), "Dynamics of Place-Exchange Reactions on Monolayer-Protected Gold Cluster Molecules.", Langmuir, 15(11): 3782-3789.
Kassam et al., (2006), "Place Exchange Reactions of Alkyl Thiols on Gold Nanoparticles.", Journal of the American Chemical Society, 128(11): 3476-3477.
Qian et al., (2008), "In vivo tumor targeting and spectroscopic detection with surface-enhanced Raman nanoparticle tags.", Nat Biotech, 26(1): 83-90.
International Preliminary Report on Patentability dated Oct. 15, 2009.
Loo, et al., 2005, Gold nanoshell bioconjugates for molecular imaging in living cells, Optic Letters, 30(9):1012-1014.
Declaration Under 37 CFR Section 1.132 by Ximei Qian.
08025US Reply to Final Office Action mailed Jul. 25, 2012.
Gao et al. In vivo cancer targeting and imaging with semiconductor quantum dots, Nature Biotechnology 22, 969-976 (2004).
Patent Examination Report No. 2, Australian Patent Application No. 2008232439, dated Sep. 5, 2014.
Patent Examination Report No. 1, Australian Patent Application No. 2008232439, dated Jan. 11, 2013.
Notice of Requisition, Canadian Patent Application No. 2,682,408, dated Jan. 20, 2015.
Examination Opinion, Chinese Patent Application No. 200880018403.1, dated Mar. 7, 2012.
Examination Opinion, Chinese Patent Application No. 200880018403.1, dated Nov. 23, 2012.
Supplemental European Search Report, European Patent Application No. 08744924.5, dated Apr. 23, 2014.

* cited by examiner

*Primary Examiner* — Michael G Hartley
*Assistant Examiner* — Sean R Donohue
(74) *Attorney, Agent, or Firm* — Emory Patent Group

(57) ABSTRACT

Nanostructures, methods of preparing nanostructures, methods of detecting targets in subjects, and methods of treating diseases in subjects, are disclosed. An embodiment, among others, of the nanostructure includes a metallic gold surface-enhanced Raman scattering nanoparticle, a Raman reporter and a protection structure. The protection structure may include a thiol-polyethylene glycol to which may be attached a target-specific probe.

18 Claims, 23 Drawing Sheets

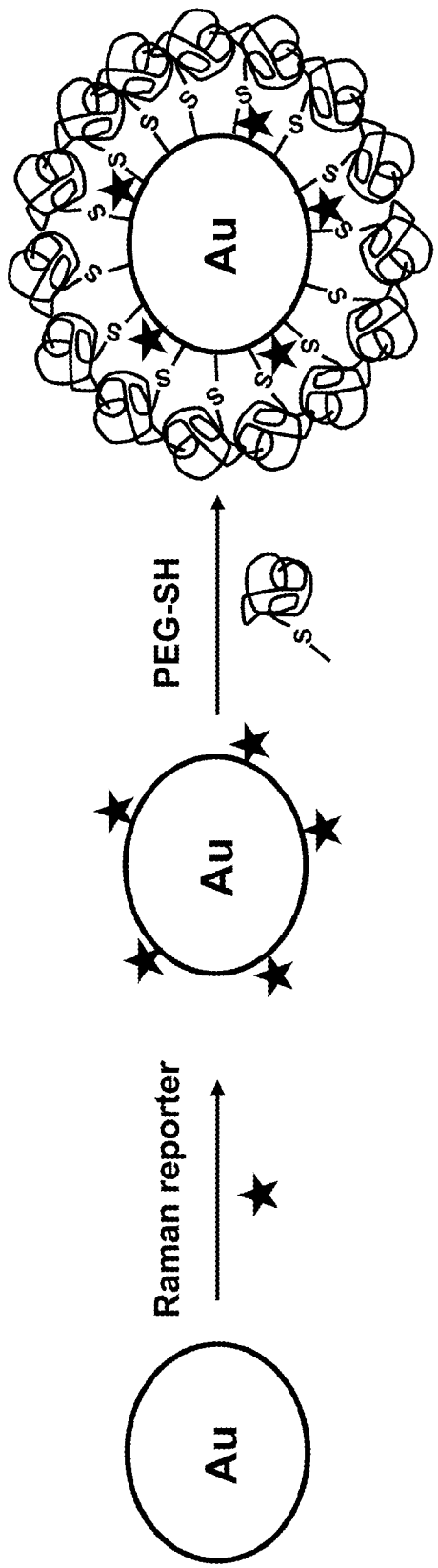

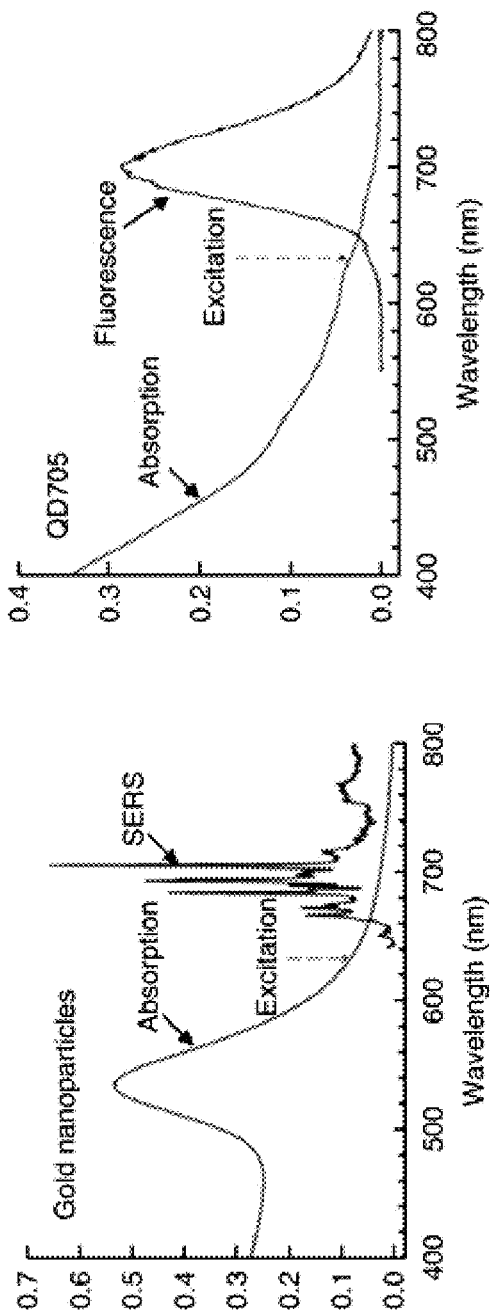

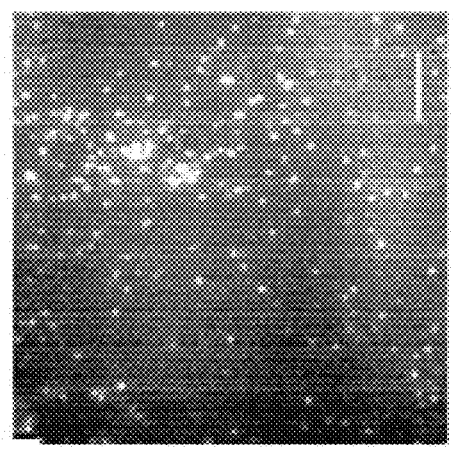
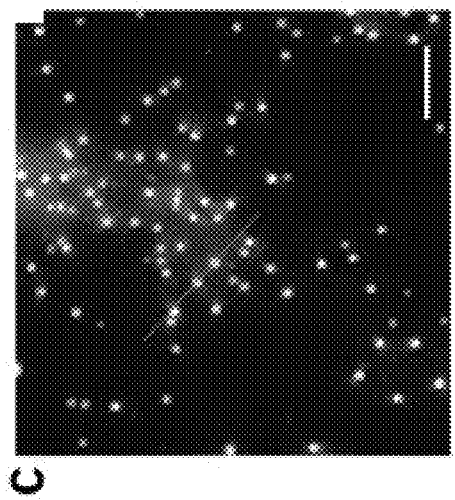
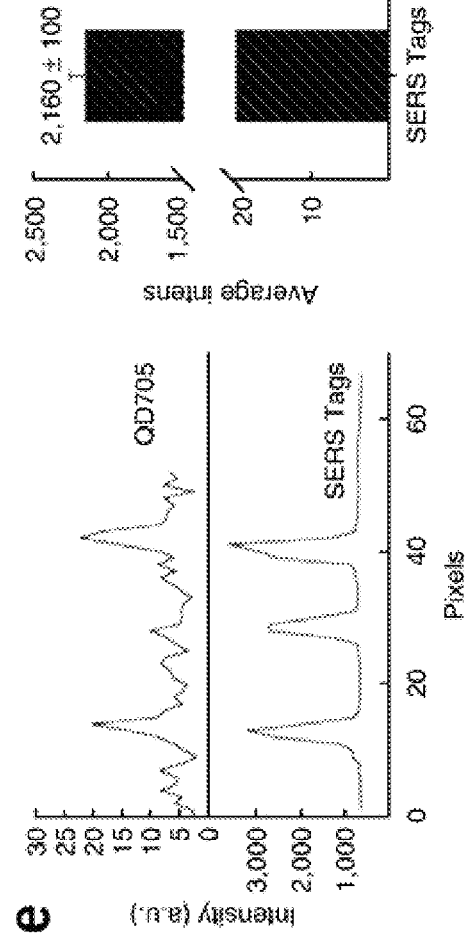
Fig. 2C
Fig. 2D
Fig. 2E
Fig. 2F

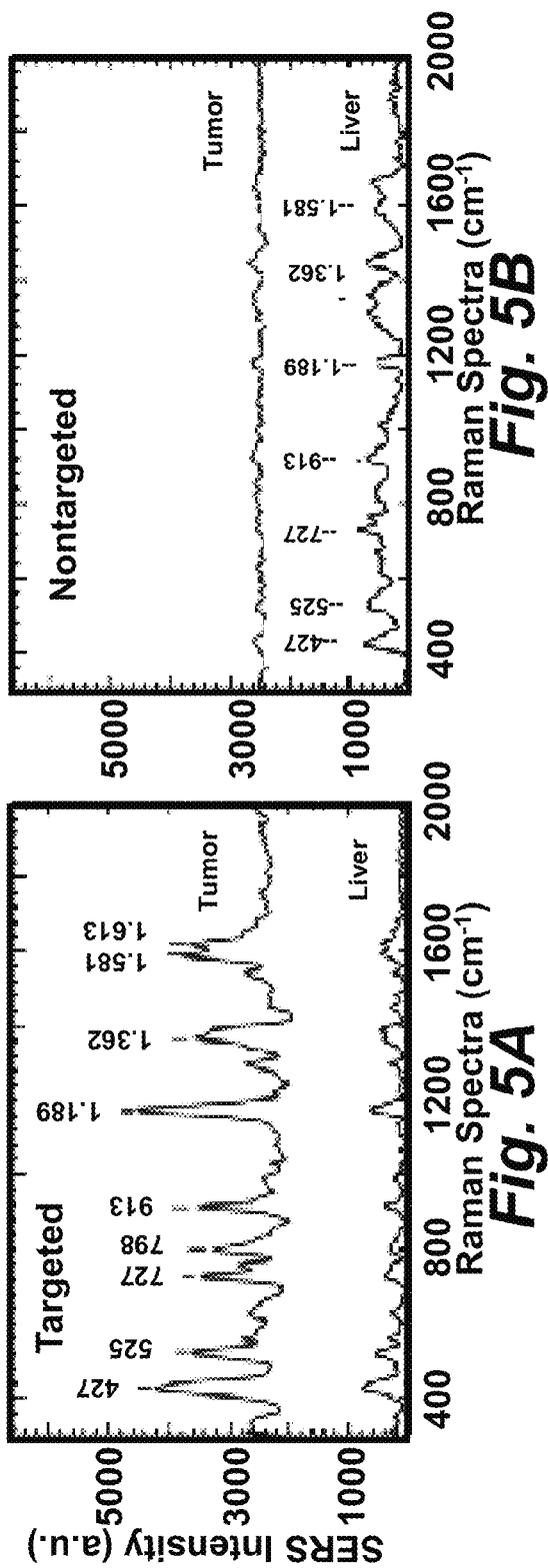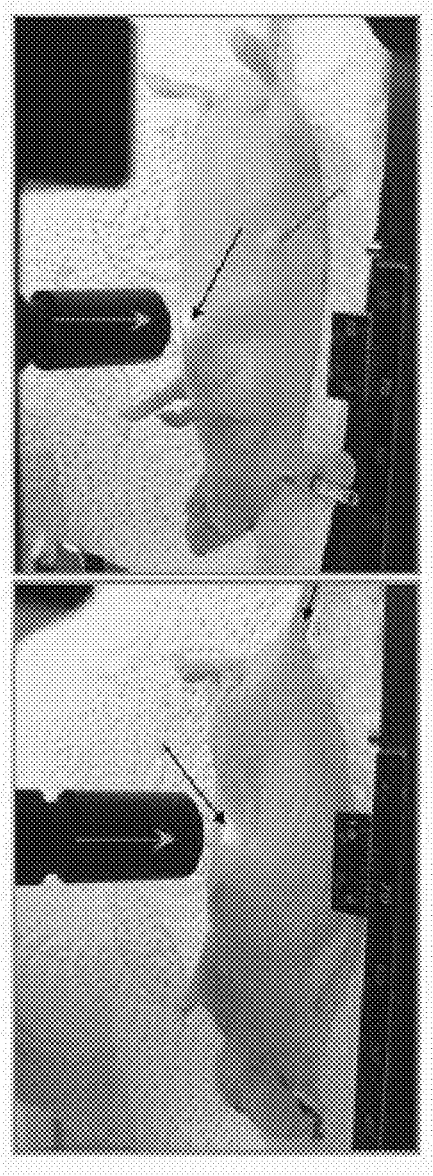
Fig. 5A  Fig. 5B  Fig. 5C

VIVO TUMOR TARGETING AND SPECTROSCOPIC DETECTION WITH SURFACE-ENHANCED RAMAN NANOPARTICLE TAGS

CROSS-REFERENCE TO RELATED APPLICATIONS

This application is a continuation application and claims priority to pending U.S. patent application Ser. No. 12/593,359 filed Sep. 28, 2009, which is a National Stage Application of international application of PCT/US2008/059117 filed Apr. 2, 2008, and claims priority to Provisional Patent Application Ser. No. 60/909,656, filed on Apr. 2, 2007, all of which are hereby incorporated by reference in their entirety.

STATEMENT REGARDING FEDERALLY SPONSORED RESEARCH OR DEVELOPMENT

This invention was made with government support under NIH Grant No. R01 CA108468 awarded by the U.S. National Institutes of Health of the United States government. The government has certain rights in the invention.

TECHNICAL FIELD

The present disclosure is generally related to surface-enhanced Raman spectroscopy nanoparticles, and cell detection uses thereof.

BACKGROUND

The development of biocompatible nanoparticles for in vivo molecular imaging and targeted therapy is an area of considerable current interest across a number of science, engineering and biomedical disciplines. The basic rationale is that nanometer-sized particles have functional and structural properties that are not available from either discrete molecules or bulk materials. When conjugated with biomolecular targeting ligands such as monoclonal antibodies, peptides or small molecules, these nanoparticles can be used to target malignant tumors with high specificity and affinity. In the 'mesoscopic' size range of 10- to 100-nm diameter, nanoparticles also have large surface areas for conjugating to multiple diagnostic (e.g., optical, radioisotopic or magnetic) and therapeutic (e.g., anticancer) agents. Recent advances have led to the development of biodegradable nanostructures for drug delivery, iron oxide nanocrystals for magnetic resonance imaging, quantum dots for multiplexed molecular diagnosis and in vivo imaging, and nanoscale carriers for short interfering RNA (siRNA) delivery.

Colloidal gold has been safely used to treat rheumatoid arthritis for half a century, and recent work indicates the pegylated gold nanoparticles (colloidal gold coated with a protective layer of polyethylene glycol or PEG) exhibit excellent in vivo biodistribution and pharmacokinetic properties upon systemic injection. In contrast to cadmium-containing quantum dots and other toxic or immunogenic nanoparticles, gold colloids have little or no long-term toxicity or other adverse effects in vivo. The discovery of single-molecule and single-nanoparticle surface-enhanced Raman scattering (SERS) has attracted considerable interest, both for fundamental studies of enhancement mechanisms and for potential applications in ultrasensitive optical detection and spectroscopy. A number of researchers have shown that the enhancement factors are as large as $10^{14}$-$10^{15}$, leading to Raman scattering cross sections that are comparable to or even larger than those of fluorescent organic dyes. This enormous enhancement allows spectroscopic detection and identification of single molecules located on the surface of single nanoparticles or at the junction of two particles at room temperature. Progress has been made concerning both the structural and mechanistic aspects of single-molecule SERS, but it is still unclear how this large enhancement effect might be exploited for applications in analytical chemistry, molecular biology, or medical diagnostics. One major problem is the intrinsic interfacial nature of SERS, which requires the molecules to adsorb on roughened metal surfaces. For biological molecules such as peptides, proteins, and nucleic acids, surface-enhanced Raman data are especially difficult to obtain, hard to interpret, and nearly impossible to reproduce.

SUMMARY

Embodiments of a new cellular imaging technology based on ultra-sensitive surface enhanced Raman scattering (SERS) spectroscopy has been developed as a diagnostic and therapeutic tool. Embodiments of the present disclosure relates to spontaneously assembled SERS nanotags with a durable and versatile protective coat for in vitro and in vivo applications. The image brightness measurements can show that the SERS nanotags are at least two orders of magnitude greater than a quantum dot tag. Bifunctional polyethylene glycol polymers serve as a linker between the gold nanoparticle core and the targeting or therapeutic agents attached to the nanostructures.

Nanoparticles, methods of preparation thereof, and methods of detecting a target molecule using embodiments of the nanoparticle, are disclosed. One embodiment of an exemplary nanoparticle, among others, includes a surface-enhanced Raman spectroscopic active composite nanostructure. The surface-enhanced Raman spectroscopic active composite nanostructure includes a core, a reporter molecule, and an encapsulating material. The reporter molecule is bonded to the core. The reporter molecule may be selected from, but is not limited to, an isothiocyanate dye, a multi-sulfur organic dye, a multi-heterosulfur organic dye, a benzotriazole dye, and combinations thereof. The encapsulating material is disposed over the core and the reporter molecule. The encapsulated reporter molecule has a measurable surface-enhanced Raman spectroscopic signature.

Briefly described, embodiments of this disclosure, among others, encompass nanostructures, methods of preparing nanostructures, methods of imaging by delivering a nanostructure of the present disclosure to a specific target on or within a cell, tissue or whole animal or human. The disclosure encompasses nanostructures that comprise a metallic nanoparticle core, a Raman reporter and a protective layer disposed thereon.

One aspect, therefore, of the disclosure encompasses surface-enhanced Raman spectroscopic active composite nanostructures comprising a core metallic nanoparticle, a Raman reporter molecule disposed on the surface of the core, and an encapsulating protective layer disposed on the surface of the core and the reporter molecule, wherein the encapsulated reporter molecule has a measurable surface-enhanced Raman spectroscopic signature.

In embodiments of the disclosure, the Raman reporter molecule may be selected from an isothiocyanate dye, a multi-sulfur organic dye, a multi-heterosulfur organic dye, a benzotriazole dye, and combinations thereof.

In embodiments of the disclosure, the reporter molecule is selected from a thiacyanine dye, a dithiacyanine dye, a thiacarbocyanine dye, and a dithiacarbocyanine dye. In other embodiments, the reporter molecule is selected from malachite green isothiocyanate, tetramethylrhodamine-5-isothiocyante, X-rhodamine-5-isothiocyanate, X-rhodamine-6-isothiocyanate, and 3,3'-diethylthiadicarbocyanine iodide.

In one embodiment of the disclosure, the core is gold, and may have a diameter less than about 200 nanometers.

In embodiments of the nanostructures of the disclosure, the encapsulating material can be a thiol-polyethylene glycol.

In other embodiments of the disclosure the nanostructures may further comprise a target-specific probe capable of selectively binding a target on a cell.

In these embodiments, the target-specific probe may be selected from the group consisting of: an antibody, a polypeptide, a polynucleotide, a drug molecule, an inhibitor compound, and a combination thereof, and wherein the targeting probe has an affinity for at least one marker on the surface of a target cell.

In one embodiment, the target-specific probe is an immunoglobulin, or a fragment thereof and in the embodiments of the disclosure the probe may be disposed on the hydrophobic protection structure. In one embodiment, the probe is a tumor-targeting ligand.

Another aspect of the disclosure encompasses methods of preparing a nanostructure according to the disclosure, comprising providing a gold nanoparticle, introducing the gold nanoparticle to a Raman reporter, whereupon the Raman reporter is disposed on the surface of the nanoparticle to form a nanoparticle-reporter complex, and disposing a protection structure layer on the surface of the nanoparticle-reporter complex, wherein the reporter molecule has a measurable surface-enhanced Raman spectroscopic signature.

In one embodiment of this aspect of the disclosure, the methods may further comprise depositing a cell target-specific probe onto the protection structure layer, wherein the probe is selected from an antibody, a polypeptide, a polynucleotide, a drug molecule, an inhibitor compound, or a combination thereof.

Yet another aspect of the disclosure encompasses methods of imaging a biological sample, comprising delivering at least one nanostructure to a cultured cell or to an animal or human subject, wherein the nanostructure comprises a core metallic, and gold, nanoparticle, a Raman reporter molecule disposed on the surface of the core, and an encapsulating protective layer disposed over the core and the reporter molecule, and wherein the encapsulated reporter molecule has a measurable surface-enhanced Raman spectroscopic signature, allowing the nanostructure to contact a targeted biological cell or tissue, exciting the reporter molecule with a source of radiation, and measuring the surface enhanced Raman spectroscopy spectrum of the nanostructure corresponding to the reporter molecule, thereby detecting the presence of the nanostructure in the targeted cell or tissue.

In one embodiment of this aspect of the disclosure, the nanostructure may further comprise a target-specific probe, wherein the targeting probe selectively binds the nanoparticle to a targeted cell, thereby allowing detection of the targeted cell.

In another embodiment of the disclosure, the target cell is in a tissue of an animal or human subject.

In the embodiments of this aspect of the disclosure, the target cell may be a cancerous cell of an animal or human subject and the target-specific probe may selected from the group consisting of an antibody, a polypeptide, a polynucleotide, a drug molecule, an inhibitor compound, and a combination thereof, and wherein the targeting probe has an affinity for a marker on the surface of a target cell.

In one embodiment of the disclosure, the target-specific probe is a tumor-targeting ligand.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates the order of preparation and schematic structures of the original gold colloid, a particle encoded with a Raman reporter, and a particle stabilized with a layer of thiol-polyethylene glycol (thiol-PEG). Approximately $1.4\text{-}1.5\times10^4$ reporter molecules (e.g., malachite green) are adsorbed on each 60-nm gold particle, which is further stabilized with $3.0\times10^4$ thiol-PEG molecules

FIGS. 2A-2F illustrate comparisons of pegylated SERS nanoparticles and near-infrared-emitting quantum dots in the spectral region of 650-750 nm.

FIGS. 2A and 2B show optical absorption and emission spectra of SERS nanoparticles (FIG. 2A) and QD705 (FIG. 2B) under identical experimental conditions.

FIG. 2C and FIG. 2D show SERS and fluorescence images of single gold nanoparticles (FIG. 2C) and single quantum dots (FIG. 2D) dispersed on glass slides and acquired under the same conditions (EM-CCD camera, 633±3 nm excitation, and 655 nm long-pass emission). The speckles shown in FIG. 2D are optical interference fringes, which become visible at low light levels.

FIG. 2E and FIG. 2F show line plots (FIG. 2E) and statistical analysis (FIG. 2F) of the brightness differences between SERS nanoparticles and quantum dots. S.D. in the Raman and quantum dot signals are indicated by error bars.

FIG. 3A shows the preparation of targeted SERS nanoparticles by using a mixture of SH-PEG and a heterofunctional PEG (SH-PEG-COOH). Covalent conjugation of an anti-EGFR-specific scFv antibody fragment occurs at the exposed terminal of the hetero-functional PEG.

FIG. 3B shows SERS spectra obtained from EGFR-positive cancer cells (Tu686) and from EGFR-negative cancer cells (human non-small cell lung carcinoma NCI-H520), together with control data and the standard tag spectrum. All spectra were taken in cell suspensions with 785-nm laser excitation and were corrected by subtracting the spectra of nanotag-stained cells by the spectra of unprocessed cells. The Raman reporter molecule is diethylthiatricarbocyanine (DTTC), and its distinct spectral signatures are indicated by wave numbers ($cm^{-1}$).

FIGS. 5A-5C illustrate in vivo cancer targeting and surface-enhanced Raman detection by using scFv-antibody conjugated gold nanoparticles that recognize the tumor biomarker EGFR.

FIGS. 5A and 5B show SERS spectra obtained from the tumor and the liver locations by using targeted (FIG. 5A) and nontargeted (FIG. 5B) nanoparticles. Two nude mice bearing human head-and-neck squamous cell carcinoma (Tu686) xenograft tumor (3-mm diameter) received 90 □l of scFv EGFR-conjugated SERS tags or pegylated SERS tags (460 pM). The particles were administered via tail vein single injection. SERS spectra were taken 5 hrs after injection.

FIG. 5C shows photographs showing a laser beam focusing on the tumor site or on the anatomical location of liver. In vivo SERS spectra were obtained from the tumor site and the liver site with 2-s signal integration and at 785 nm excitation. The spectra were background subtracted and shifted for better visualization. The Raman reporter molecule is malachite green, with distinct spectral signatures as labeled in FIGS. 5A and 5B. The laser power is about 20 mW.

Figure 1B:
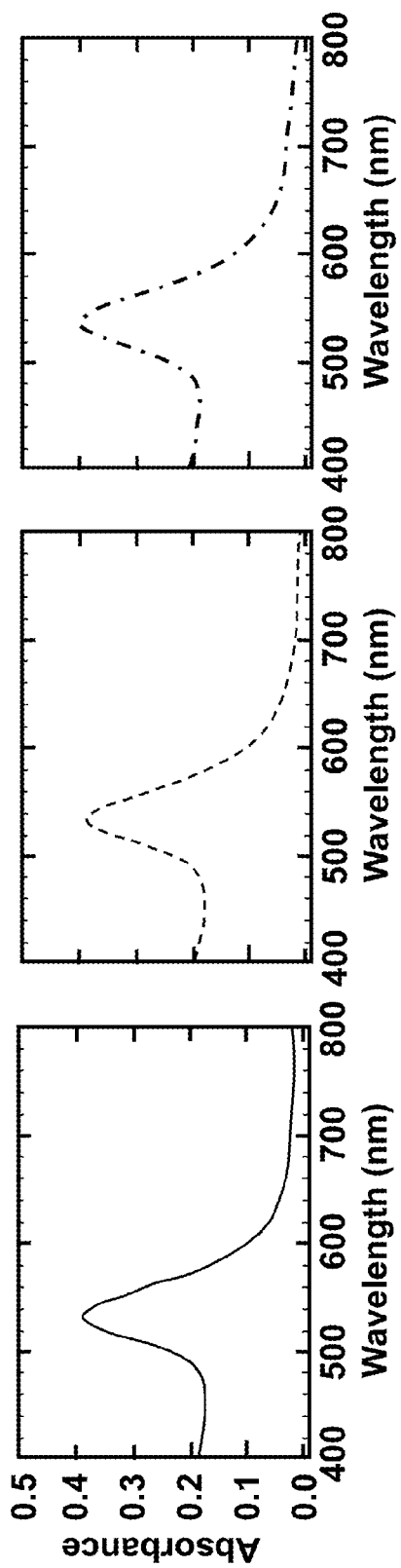
FIG. 1B illustrates the optical absorptions obtained from the original, Raman-encoded, and PEG-stabilized gold nanoparticles shown in FIG. 1A.
Figure 1C:
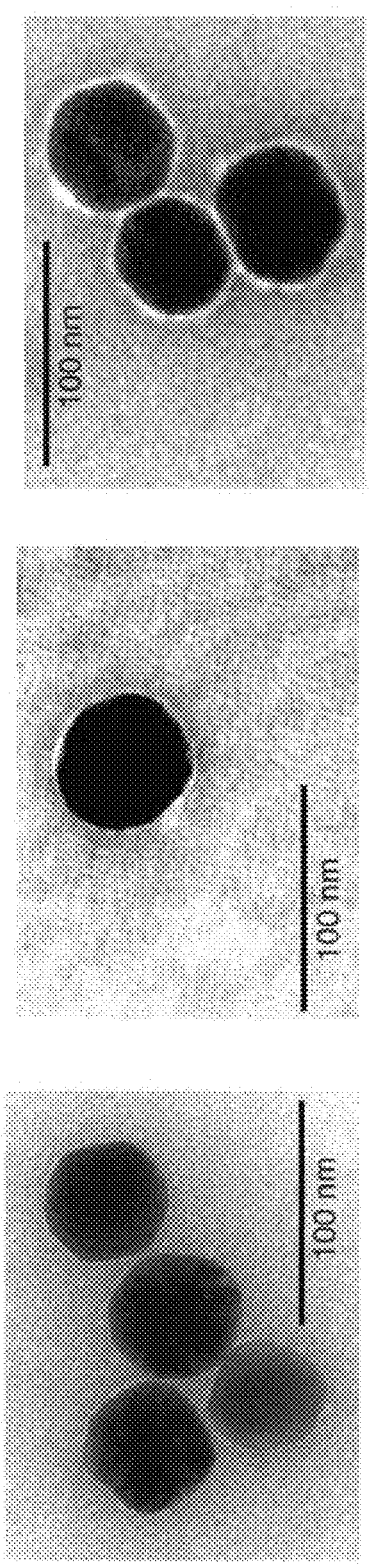
FIG. 1C illustrates the transmission electron microscopy (TEM) obtained from the original, Raman-encoded, and PEG-stabilized gold nanoparticles shown in FIG. 1A.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

The term "Raman light scattering" as used herein refers to when certain molecules are illuminated, a small percentage of the molecules which have retained a photon do not return to their original vibrational level after remitting the retained photon, but drop to a different vibrational level of the ground electronic state. The radiation emitted from these molecules will therefore be at a different energy and hence a different wavelength. This is referred to as Raman scattering.

If the molecule drops to a higher vibrational level of the ground electronic state, the photon emitted is at a lower energy or longer wavelength than that absorbed. This is referred to as Stokes-shifted Raman scattering. If a molecule is already at a higher vibrational state before it absorbs a photon, it can impart this extra energy to the remitted photon thereby returning to the ground state. In this case, the radiation emitted is of higher energy (and shorter wavelength) and is called anti-Stokes-shifted Raman scattering. In any set of molecules under normal conditions, the number of molecules at ground state is always much greater than those at an excited state, so the odds of an incident photon interacting with an excited molecule and being scattered with more energy than it carried upon collision is very small. Therefore, photon scattering at frequencies higher than that of the incident photons (anti-Stokes frequencies) is minor relative to that at frequencies lower than that of the incident photons (Stokes frequencies). Consequently, it is the Stokes frequencies that are usually analyzed.

The term "surface enhanced Raman scattering (SERS)" as used herein refers to a significant increase in the intensity of Raman light scattering that can be observed when molecules are brought into close proximity to (but not necessarily in contact with) certain metal surfaces. The metal surfaces need to be "roughened" or coated with minute metal particles.

Metal colloids also show this signal enhancement effect. The increase in intensity can be on the order of several million-fold or more. The cause of the SERS effect is not completely understood; however, current thinking envisions at least two separate factors contributing to SERS. First, the metal surface contains minute irregularities. These irregularities can be thought of as spheres (in a colloid, they are spheroidal or nearly so). Those particles with diameters of approximately $\frac{1}{10}$th the wavelength of the incident light were considered to contribute most to the effect. The incident photons induce a field across the particles which, being metal, have very mobile electrons.

In certain configurations of metal surfaces or particles, groups of surface electrons can be made to oscillate in a collective fashion in response to an applied oscillating electromagnetic field. Such a group of collectively oscillating electrons is called a "plasmon." The incident photons supply this oscillating electromagnetic field. The induction of an oscillating dipole moment in a molecule by incident light is the source of the Raman scattering. The effect of the resonant oscillation of the surface plasmons is to cause a large increase in the electromagnetic field strength in the vicinity of the metal surface. This results in an enhancement of the oscillating dipole induced in the scattering molecule and hence increases the intensity of the Raman scattered light. The effect is to increase the apparent intensity of the incident light in the vicinity of the particles.

A second factor considered to contribute to the SERS effect is molecular imaging. A molecule with a dipole moment, which is in close proximity to a metallic surface, will induce an image of itself on that surface of opposite polarity (i.e., a "shadow" dipole on the plasmon). The proximity of that image is thought to enhance the power of the molecules to scatter light. This coupling of a molecule may have an induced or distorted dipole moment to the surface plasmons greatly enhances the excitation probability. The result is a very large increase in the efficiency of Raman light scattered by the surface-absorbed molecules.

The SERS effect can be enhanced through combination with the resonance Raman effect. The surface-enhanced Raman scattering effect is even more intense if the frequency of the excitation light is in resonance with a major absorption band of the molecule being illuminated. The resultant Surface Enhanced Resonance Raman Scattering (SERRS) effect can result in an enhancement in the intensity of the Raman scattering signal of seven orders of magnitude or more.

The term "Raman reporter" as used herein can refer to small organic compounds such as thiophenol, mercaptobenzoic acid, and bispyridine previously used as Raman spectroscopic reporters. These molecules give rise to simple Raman spectra, but it has been difficult or impossible to achieve resonance Raman enhancement at visible excitation wavelengths. As a result, the reported SERS intensities are relatively low, even at high (millimolar) reporter concentrations. Organic dyes with an isothiocyanate (—N=C=S) group or with multiple sulfur atoms adsorb strongly on the core particles and may be compatible with encapsulation. For example, intense SERS spectra have been obtained from (b) malachite green isothiocyanate (MGITC), (c) tetramethylrhodamine-5-isothiocyanate TRITC), (d) X-rhodamine-5- (and -6)-isothiocyanate (XRITC), and (a) 3,3'-diethylthiadicarbocyanine iodide (DTDC). Three of these molecules contain an isothiocyanate group, while the fourth has two sulfur atoms in ring structures.

The isothiocyanate group or sulfur atoms provide an "affinity tag" for binding to gold surfaces, yielding a sulfur-gold bond that is stable. For molecules without such an affinity tag such as crystal violet and rhodamine 6G, intense SERS spectra may be observed, but the signals disappeared after, for example, silica coating. In addition, most of these dyes have strong electronic transitions in the visible spectrum, so resonance Raman enhancement can be used to further increase the signal intensities. In a strict sense, these molecules should be called "resonant Raman reporters," to distinguish them from thiophenol and other nonresonant Raman reporters. In most cases, resonance Raman provides about 2-3 orders of magnitude of additional enhancement relative to surface enhancement alone. Both fluorescent and nonfluorescent dyes can be used as resonant Raman reporters because fluorescence emission is efficiently quenched by the gold particles, not interfering with Raman measurement. A series of benzotriazole dyes are excellent for surface-enhanced resonance Raman scattering; due to the presence of multiple nitrogen atoms, these molecules could provide a new class of resonant Raman reporters for spectroscopic encoding and multiplexing applications.

The term "protective layer" as used herein refers to a layer that may totally or partially encapsulate a nanoparticle, thereby preventing aggregation of the particles. The biocompatible layer may comprise, but is not limited to, a thiol-polyethylene glycol polymer, wherein the thiol group links the polymer to the underlying nanoparticle. The distal end of the polymer may have a reactive group to which a target-specific ligand may be coupled. The protective layer may be disposed, i.e., located or deposited on or around, in whole or in part, the surface of the metallic nanoparticle and reporter nanostructure.

The term "quantum dot" (QDs) as used herein refers to semiconductor nanocrystals or artificial atoms, which are semiconductor crystals that contain anywhere between 100 to 1,000 electrons and range from about 2-10 nm. Some QDs can be between about 10-20 nm in diameter. QDs have high quantum yields, which makes them particularly useful for optical applications. QDs are fluorophores that fluoresce by forming excitons, which can be thought of the excited state of traditional fluorophores, but have much longer lifetimes of up to 200 nanoseconds. This property provides QDs with low photobleaching.

The terms "polypeptide" or "protein" as used herein are intended to encompass a protein, a glycoprotein, a polypeptide, a peptide, and the like, whether isolated from nature, of viral, bacterial, plant, or animal (e.g., mammalian, such as human) origin, or synthetic, and fragments thereof. A preferred protein or fragment thereof includes, but is not limited to, an antigen, an epitope of an antigen, an antibody, or an antigenically reactive fragment of an antibody.

The term "nucleic acid" as used herein refers to DNA and RNA, whether isolated from nature, of viral, bacterial, plant or animal (e.g., mammalian, such as human) origin, synthetic, single-stranded, double-stranded, comprising naturally or non-naturally occurring nucleotides, or chemically modified.

The term "cancer", as used herein shall be given its ordinary meaning and is a general term for diseases in which abnormal cells divide without control. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer.

Cardiovascular disease, as used herein, shall be given its ordinary meaning, and includes, but is not limited to, high blood pressure, diabetes, coronary artery disease, valvular heart disease, congenital heart disease, arrthymia, cardiomyopathy, CHF, atherosclerosis, inflamed or unstable plaque associated conditions, restinosis, infarction, thromboses, post-operative coagulative disorders, and stroke.

Inflammatory disease, as used herein, shall be given its ordinary meaning, and can include, but is not limited to, autoimmune diseases such as arthritis, rheumatoid arthritis, multiple sclerosis, systemic lupus erythematosus, other diseases such as asthma, psoriasis, inflammatory bowel syndrome, neurological degenerative diseases such as Alzheimer's disease, Parkinson's disease, Huntington's disease, vascular dementia, and other pathological conditions such as epilepsy, migraines, stroke and trauma.

DESCRIPTION

In accordance with the purpose(s) of the present disclosure, as embodied and broadly described herein, embodiments of the present disclosure encompass surface-enhanced Raman spectroscopic (SERS) active composite nanostructures, methods of fabricating these nanostructures, and methods of using these nanostructures. The SERS active composite nanostructures are distinguishable and can be individually detected. In this regard, the SERS active composite nanostructures can be modified so that the SERS active composite nanostructures interact with certain target molecules, which allow detection of the target molecules. In addition, the SERS active composite nanostructures can be used in encoding systems as well as in multiplexing systems. The SERS active composite nanostructures can be used in many areas such as, but not limited to, flow cytometry, chemical array systems, biomolecule array systems, biosensing, biolabeling, high-speed screening, gene expression studies, protein studies, medical diagnostics, diagnostic libraries, and microfluidic systems.

The SERS active composite nanostructures provided by the present disclosure include, but are not limited to, a core, a reporter molecule disposed thereon, and an encapsulant protective material or layer. In an embodiment, the core material is a metal. In an embodiment the core is gold or silver. In an embodiment the core is gold. The reporter molecules may be disposed (bonded) onto the core, while the encapsulant material covers and protects the core and reporter molecules. On the hydrophilic protective surface of SERS nanostructures according to the present disclosure, there may be a large number of functional groups that may be derivatized and may allow the attachment of both diagnostic and therapeutic agents or target-specific probes. With small-molecule ligands such as synthetic organic molecules, short oligonucleotides and peptides, many copies of the same ligand can be linked to single nanoparticles, leading to multivalent SERS-nanoparticle-target binding.

Such nanoparticles may each comprise a SES-active metal nanoparticle, a submonolayer, monolayer, or multilayer of spectroscopy-active species in close proximity to the metal surface, and an encapsulating protective shell. This places the spectroscopy-active molecule (the "reporter") at the interface between the metal nanoparticle and the encapsulant. In a typical and advantageous embodiment, a SERS nanostructure comprises (i) a metal nanoparticle core (e.g., gold or silver), (ii) a Raman-active reporter, that gives a unique vibrational signature, and (iii) protective encapsulant that "locks" the reporter molecules in place while also providing a highly biocompatible surface. The protective coating, which is essentially SERS-inactive, also stabilizes the particles against aggregation and prevents competitive adsorption of unwanted species.

Although not intending to be bound by theory, the core optically enhances the SERS spectrum, while the reporter molecule provides a distinct spectroscopic SERS signature. Disposing the encapsulant material over the core and reporter molecule does not substantially impact the spectroscopic SERS signature of the reporter molecule, while protecting the core and reporter molecules. Unlike other SERS particles, the SERS active composite nanostructure described in the present disclosure have strong SERS intensities (more than about 10,000 counts with 1 mW laser power in about a second). In some embodiments, the SERS active composite nanostructure have measurable surface-enhanced resonance Raman spectroscopic signatures.

The class of core-shell colloidal nanoparticles (e.g., SERS active composite nanostructures) that are highly efficient for SERS and herein disclosed are suitable for multiplexed detection and spectroscopy at the single-particle level. With nearly optimized gold cores and protective shells, the SERS active composite nanostructures of this disclosure are stable in both aqueous electrolytes and organic solvents, and yield intense single-particle SERS spectra. Blinking or intensity fluctuation is still observed, indicating that the SERS signals could arise from single molecules at the interface between the core and the shell. A surprising finding is that organic dyes with an isothiocyanate ($-N=C=S$) group or multiple sulfur atoms are compatible with the encapsulation process, and are an excellent group of Raman reporters due to their rich vibrational spectra and the possibility of combined surface enhancement and resonance enhancement.

In contrast to most previous SERS studies, the surface enhanced Raman signals reported here do not come from the target molecules, but from a reporter dye that is embedded in the SERS active composite nanostructures. This design avoids the problems of, among other things, surface adsorption, substrate variations, and poor data reproducibility. This development has opened new possibilities in using SERS for spectroscopic labeling of multiple biomarkers in single cells and tissue specimens, including Raman-activated flow cytometry and cell sorting. In comparison with other biolabels such as fluorescent dyes and semiconductor quantum dots, SERS active composite nanostructures contain a built-in mechanism for signal enhancement and provide rich spectroscopic information in ambient conditions. Furthermore, the extremely short lifetimes of Raman scattering prevent photobleaching, energy transfer, or quenching in the excited state.

The nanoparticle core may be a metallic nanoparticle known in the art. As used herein, the term "nanoparticle", "nanostructure", "nanocrystal", "nanotag," and "nanocomponent" are used interchangeably to refer to a metallic particle with or without additional layers such as an encapsulating protective layer, having one dimension from about 1 nm to 1000 nm, including any integer value between about 1 nm and 1000 nm. In some embodiments, the metal nanoparticle core can be a spherical or nearly spherical particle of about 20-200 nm in diameter. In some embodiments the range is about 2 nm to 50 nm, in some embodiments in the range of about 20 nm to 50 nm. Anisotropic nanoparticles may have a length and a width. In some embodiments, the length of an anisotropic nanoparticle is the dimension parallel to the aperture in which the nanoparticle was produced. In the case of anisotropic nanoparticles, in some embodiments, the nanoparticle can have a diameter (width) of about 350 nm or less. In other embodiments, the nanoparticle can have a diameter of about 250 nm or less and in some embodiments, a diameter of about 100 nm or less. In some embodiments, the width can be about 15 nm to 300 nm. In some embodiments, the nanoparticle can have a length of about 10-350 nm.

Nanoparticles may be isotropic or anisotropic. Nanoparticles include colloidal metal hollow or filled nanobars, magnetic, paramagnetic, conductive or insulating nanoparticles, synthetic particles, hydrogels (colloids or bars), and the like. It will be appreciated by one of ordinary skill in the art that nanoparticles can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

The reporter molecule can include molecules such as, but not limited to, organic dye molecules having an isothiocyanate group (hereinafter "isothiocyanate dyes"), organic dye molecules having two or more sulfur atoms (hereinafter "multi-sulfur organic dyes"), organic dye molecules having two or more heterocyclic rings each incorporating sulfur atoms (hereinafter "multi-heterosulfur organic dyes"), and benzotriazole dyes. In addition, the reporter molecule may include resonant Raman reporters, which have strong electronic transitions in the visible spectrum, so that resonance Raman enhancement can be used to further amplify the signal intensities. The resonant Raman reporters include, but are not limited to, organic dyes, biomolecules, porphyrins, and metalloporphyrins. In particular, the resonant Raman reporters can include, but are not limited to, malachite green isothiocyanate, tetramethylrhodamine-5-isothiocyante, X-rhodamine-5-isothiocyanate, X-rhodamine-6-isothiocyanate, 3,3'-diethylthiadicarbocyanine iodide, and combinations thereof. A particularly advantageous reporter molecule is malachite green.

Further, the reporter molecule can include, but is not limited to, thiacyanine dyes, dithiacyanine dyes, thiacarbocyanine dyes (e.g., thiacarbocyanine dyes, thiadicarbocyanine dyes, and thiatricarbocyanine dyes), and dithiacarbocyanine dyes (e.g., dithiacarbocyanine dyes, dithiadicarbocyanine dyes, and dithiatricarbocyanine dyes), and combinations thereof.

Furthermore, the reporter molecule can include: 3,3'-diethyl-9-methylthiacarbocyanine iodide; 1,1'-diethyl-2,2' quinotricarbocyanine iodide; 3,3'-diethylthiacyanine iodide; 4-acetamido-4'-isothiocyanatostilbene-2,2'-disulfonic acid, disodium salt; benzophenone-4-isothiocyanate; 4,4'-diisothiocyanatodihydrostilbene-2,2'-disulfonic acid, disodium salt; 4,4'-diisothiocyanatostilbene-2,2'-disulfonic acid, disodium salt; N-(4-(6-dimethylamino-2-benzofuranyl)phenylisothiocyanate; 7-dimethylamino-4-methylcoumarin-3-isothiocyanate; eosin-5-isothiocyanate; erythrosin-5-isothiocyanate; fluorescein-5-isothiocyanate; (S)-1-p-isothiocyanatobenzyldiethylenetriaminepentaacetic acid; Oregon Green® 488 isothiocyanate; tetramethylrhodamine-5-isothiocyanate; tetramethylrhodamine-6-isothiocyanate; tetramethylrhodamine-5-(and -6)-isothiocyanate; X-rhodamine-5-(and -6)-isothiocyanate, and combinations thereof.

The benzotriazole dyes can include, but are not limited to, azobenzotriazoyl-3,5-dimethoxyphenylamine, and dimethoxy-4-(6'-azobenzotriazolyl)phenol.

As mentioned above, the reporter molecules can have an isothiocyanate group or two or more sulfur atoms (e.g., isothiocyanate dyes, multi-sulfur organic dyes, and multi-heterosulfur organic dyes) that are capable of forming sulfur-gold bonds that are stable against deposition of the coupling agent and the encapsulant material. In addition, these reporter molecules have strong electronic transitions in the visible and near-infrared spectra (about 400-850 nm), so that resonance Raman enhancement can be used to increase signal intensity.

The SERS active composite nanostructure advantageously may have a spherical diameter or substantially spherical diameter of less than about 250 nanometers (nm), about 10 to 150 nm, and about 30 to 90 nm. The core diameter can be about 10 to 200 nm, about 20 to 100 nm, and about 40 to 80 nm. The encapsulant thickness can be about 1 to 50 nm, about 2 to 50 nm, and about 5 to 10 nm. In general, the greater the encapsulant diameter, the better the protection that is provided. With increased diameter, however, the overall size of the SERS active composite nanostructure increases. Selection of the appropriate dimensions can be determined based on the particular application.

In general, the reporter molecule can cover about 1 to 75% of the surface of the core (e.g., the reporter molecule adsorbs onto about 1 to 75% of the core particle surface), about 15 to 50% of the surface of the core 12, about 15 to 30% of the surface of the core 12, and about 20 to 25% of the surface of the core 12.

In embodiments including coupling agents, the coupling agent can cover about 1 to 100% of the surface of the core, about 40 to 60% of the surface of the core 12, and about 45 to 50% of the surface of the core. In an embodiment the reporter molecule can cover about 1 to 75% of the surface of the core, about 15 to 50% of the surface of the core 12, about 15 to 30% of the surface of the core 12, and about 20 to 25% of the surface of the core.

The SERS active composite nanostructure can be prepared in one or more ways. For example, the SERS active composite nanostructure can be prepared by mixing the core with the reporter molecule under conditions such that the reporter molecule bonds to the core. In particular, the core may be mixed with reporter molecules having a concentration from about $2.5 \times 10^{-8}$ M to $1.25 \times 10^{-7}$ M and about $7.5 \times 10^{-8}$ M for about 1 to 30 minutes. Then, in one embodiment, a coupling agent is mixed with the core having reporter molecules disposed thereon. In particular, the coupling agent may be added to a final concentration of about $2.5 \times 10^{-7}$ M for about 1 to 30 minutes. Subsequently, the core having reporter molecules disposed thereon (and in some embodiments having coupling agents disposed thereon) may be mixed with the encapsulating material at a pH of about 9 to 11 for about 24 to 96 hours. Additional details regarding the preparation of the SERS active composite nanostructure are described in the examples presented herein.

The present disclosure encompasses the use of a protective capsule disposed on the surface of the core-Raman reporter complex. It is contemplated that a variety of materials may be used to encapsulate the core-reporter. Most advantageously, the protective layer comprises a thiol-polyethylene glycol, whereby the polymer is coupled to the underlying core by means of the thiol group. The distal end of the polymer may comprise an active group such as, but not limited to, a carboxyl or amine group that may form a coupling to a target-specific entity such as, but not limited to an immunoglobulin or a fragment thereof.

The SERS active composite nanostructure can be attached to a probe molecule. The SERS active composite nanostructure can also be attached to a structure (e.g., in an assay) or float freely (e.g., in a microfluidic system or in flow cytometry). The probe molecule can be any molecule capable of being linked to the SERS active composite nanostructure either directly, or indirectly via a linker. For example, the target-specific probe may be attached to the protective encapsulating material such as thiol-polyethylene glycol. The probe molecule can be attached to the SERS active composite nanostructure by a stable physical and/or chemical association.

The advantageous target-specific probe molecules contemplated for use in the embodiments of the present disclosure may have an affinity for one or more target molecules for which detection is desired. If, for example, the target molecule is a nucleic acid sequence, the probe molecule should be chosen so as to be substantially complementary to the target molecule sequence, such that the hybridization of the target and the probe occurs. The term "substantially complementary," means that the probe molecules are sufficiently complementary to the target sequences to hybridize under the selected reaction conditions.

In one embodiment, the probe molecule has an affinity for one or more target molecules (e.g., cancer cell) for which detection (e.g., determining the presence of and/or proximal position within the vessel (body)) is desired. If, for example, the target molecule is a nucleic acid sequence, the probe molecule should be chosen so as to be substantially complementary to the target molecule sequence, such that the hybridization of the target and the probe occurs. The term "substantially complementary," means that the probe molecules are sufficiently complementary to the target sequences to hybridize under the selected reaction conditions.

The probe molecule and the target molecule can include, but are not limited to, polypeptides (e.g., protein such as, but not limited to, an antibody (monoclonal or polyclonal)), nucleic acids (both monomeric and oligomeric), polysaccharides, sugars, fatty acids, steroids, purines, pyrimidines, drugs (e.g., small compound drugs), ligands, or combinations thereof. Advantageously, the probe may be an antibody or a ligand compatible with, and capable of binding to, a target molecule on the surface of a cell such as, but not limited to, a cancer cell.

The nanostructures of the disclosure can include at least two different types of probes, each being, for example, a targeting probe that targets certain cells.

The present disclosure provides methods of targeting one or more target cells in a sample or a subject (e.g., mammal, human, cat, dog, horse, etc.). For example, the nanostructure can be used to detect tumor cells in an animal using the nanostructures according to the present disclosure.

It should also be noted that nanostructures could be used for the detection of, as part of treatment of (e.g., drug delivery), as an indication of delivery to one or more targets (e.g., cancers), or combinations thereof, conditions and/or diseases such as, but not limited to, cancers, tumors, neoplastic diseases, autoimmune diseases, inflammatory diseases, metabolic conditions, neurological and neurodegenerative diseases, viral diseases, dermatological diseases, cardiovascular diseases, an infectious disease, and combinations thereof.

It should be noted that a cell can be pre-labeled (e.g., in vitro and in vivo) with nanostructures and/or microstructures. For example, cells can be labeled with nanoparticle-block copolymer microstructures in vitro through immunostaining, adsorption, microinjection, cell uptake, and the like. The cells then can be monitored in vitro, or traced in vivo with the nanoparticles as a tracer, fluorescence, magnetic, combinations thereof, and the like, while the expression of a gene may be modified by a probe attached to the outer surface of the SERS nanostructures.

The present disclosure provides a method of detecting one or more target molecules in a sample. The method includes attaching a target molecule (e.g., via a target-specific probe molecule) to the nanostructure and measuring the SERS spectrum of the nanostructure, where the detection of SERS spectrum specific for the reporter molecule indicates the presence of the target molecule specific for the probe molecule. The SERS active composite nanostructure can be used to detect the presence of one or more target molecules in chemical array systems and biomolecular array systems. In addition, SERS active composite nanostructures can be used to enhance encoding and multiplexing capabilities in various types of systems.

In one embodiment, a flow cytometer can be used in multiplexed assay procedures for detecting one or more target molecules using one or more SERS active composite nanostructure. Flow cytometry is an optical technique that analyzes particular particles (e.g., SERS active composite nanostructures) in a fluid mixture based on the particles' optical characteristics. Flow cytometers hydrodynamically focus a fluid suspension of SERS active composite nanostructures into a thin stream so that the SERS active composite nanostructures flow down the stream in substantially single file and pass through an examination zone. A focused light beam, such as a laser beam, illuminates the SERS active composite nanostructures as they flow through the examination zone. Optical detectors within the flow cytometer measure certain characteristics of the light as it interacts with the SERS active composite nanostructures. Commonly used flow cytometers can measure SERS active composite nanostructure emission at one or more wavelengths.

One or more target molecules can be detected using a SERS active composite nanostructure and one or more probes having an affinity for one or more of the target molecules. Each SERS active composite nanostructure has a reporter molecule that corresponds to the probe. Prior to being introduced to the flow cytometer, the SERS active composite nanostructures specific for certain target molecules are mixed with a sample that may include one or more target molecules. The SERS active composite nanostructures interact with (e.g., bond or hybridize) the corresponding target molecules for which the probe has an affinity.

Next, the SERS active composite nanostructures are introduced to the flow cytometer. As discussed above, the flow cytometer is capable of detecting the SERS active composite nanostructure after exposure to a first energy. Detection of a certain Raman spectrum corresponding to a certain reporter molecule indicates that a target molecule is present in the sample.

Images of cells containing Raman spectral information can be obtained by a number of methods. A microscope can be coupled to a CCD camera such that complete images of the object may be obtained. Then, between the sample and the camera, a wavenumber filtering device such as a monochromator or liquid crystal tunable filter is inserted. The filtering device only allows a narrow bandwidth of the scattered radiation to reach the camera at any one time. Multiple images are collected, each covering a small spectral range of the scattered radiation. The spectra from each point in the image are assembled in software. At the other extreme, light from a single point of an image may be dispersed through a monochromator and the complete spectrum of that point can be acquired on an array detector. The object is then scanned such that each point in the image is acquired separately. The Raman image is then assembled in software. In another approach, a line scan instrument can be constructed that excites the sample with a line of radiation. The line is imaged spatially along one axis of a CCD camera while simultaneously being spectrally dispersed along the orthogonal axis. Each readout of the camera acquires the complete spectrum of each spatial pixel in the line. To complete the image the line is scanned across the sample.

Thus, according to this disclosure, cells or cell populations may be identified by using an antibody-conjugated SERS nanostructure prepared with an antibody that may bind a cell surface antigenic receptor expressed on a cell subpopulation.

SERS nanostructures according to the present disclosure may also be used to detect intracellular targets. SERS nanostructures may be introduced into cells via microinjection, electroporation, endocytosis-mediated approaches including the use of amphipathic peptides such as PEP-1, the use of cationic lipid-based reagents, such as Lipofectamine (Invitrogen), and the use of micelles and transfection reagents such as transferrin, mannose, galactose, and Arg-Gly-Asp (RGD), and other reagents such as the dendrimer-based reagent SuperFect (Qiagen).

Intracellular indirect methods can be used to prove that the particles are bound to the desired targets. The simplest method to demonstrate the specificity of the probes is to use immunofluorescence to verify the location of the SERS nanostructures. There are a number of commercially available fluorescent probes that are useful for labeling cellular structures (such as the mitochondria, Golgi apparatus and endoplasmic reticulum) in living cells. By conjugating an antibody that targets the same structure, what fraction of particles is actively labeling their target can be determined; and what percentage are non-specifically bound. Another approach to verifying the location of the SERS nanostructures is to use fluorescent protein fusions, such as GFP and its analogs.

The present disclosure, therefore, encompasses nanostructures directed to imaging agents displaying important properties in medical diagnosis. More particularly, the present disclosure is directed to imaging agents comprising SERS nanostructures. The imaging agents of the present disclosure are useful in imaging a patient generally, and/or in specifically diagnosing the presence of diseased tissue in a patient. By choice of composition, the excitation and emission of SERS nanostructures can be tuned to occur between about 633 nm and 1000 nm, in the minimum region for absorption and scattering by tissues. The imaging process may be carried out by administering an imaging agent of the disclosure to a patient, and then scanning the patient using any system that can perform spectral imaging, such as spot scanning confocal microscopes, line scanning systems, and Optical Coherence tomographic systems. SERS nanostructures of the present disclosure can also be seen by any imaging system that detects only over a single wavelength band, the list above as well as any fluorescence imaging system that has an excitation light source and filtered image detection. Also included are time domain methods, such as dynamic light scattering spectroscopy and tomography, time-of-flight imaging, quasi-elastic light scattering spectroscopy, photon-correlation spectroscopy, Doppler spectroscopy, and diffusion wave spectroscopy. All these techniques allow differentiation between photons and where they have been based on their time signatures. Since SERS nanostructures will have different time signatures than fluorescent substances, etc., they can be discriminated against tissues and other labels with these methods. Useful instrument parameters are a modulated light source and time sensitive detector. Modulation can be pulsed or continuous.

The scanning results in spectra or images of an internal region of a patient and/or of any-diseased tissue in that region. By region of a patient, it is meant the whole patient, or a particular area or portion of the patient. The imaging agent may be employed to provide images of the vasculature, heart, liver, and spleen, and in imaging the gastrointestinal region or other body cavities, or in other ways as will be readily apparent to those skilled in the art, such as in tissue characterization, blood pool imaging. etc.

This disclosure also provides a method of diagnosing abnormal pathology in vivo comprising, introducing a plurality of SERS nanostructures targeted to a molecule involved in the abnormal pathology into a bodily fluid contacting the abnormal pathology, wherein the SERS nanostructures become associated to a molecule involved in the abnormal pathology, and imaging the associated SERS nanostructures in vivo. The method is generally applicable to any organ accessible by the probes: gastro-intestinal tract, heart, lung, liver cervix, breast, etc. In some embodiments, the SERS nanostructures can be introduced via an endoscope, as in the case of a colonoscopy, or a needle, or used with a disposable tip or sleeve. In other embodiments, the SERS nanostructures may be introduced by directly by the imaging probe itself. For example, individual optical fibers, or bundles of optical fibers, can be introduced into live organisms for imaging, and has been demonstrated for imaging of nerves, brain, microvessels, cells, as well as for characterizing biodistribution. Gel-coated optical fibers are very well known in the sensor literature. SERS nanostructures can be non-covalently bound to the gel, diffusing into the relevant tissue upon introduction. A variety of other methods to immobilize SERS nanostructures onto the outer surface of fibers such that they diffuse into liquid phases to which they are contacted can be envisioned.

The present disclosure also provides method for labeling an animal with SERS nanostructures, comprising introducing SERS nanostructures into an animal. SERS nanostructures can be introduced into animals by any suitable means, such as by subcutaneous implantation or intravenously, and detected using appropriate equipment. The present disclosure also provides an identification system and related methods for animals such as livestock or house pets by utilizing SERS nanostructures implanted under the hide or skin to identify the animal.

Under in vivo conditions, nanostructures according to the disclosure can be delivered to tumors by both a passive targeting mechanism and an active targeting mechanism. In the passive mode, macromolecules and nanometer-sized particles are accumulated preferentially at tumor sites through an enhanced permeability and retention (EPR) effect. This effect is believed to arise from two factors: (a) angiogenic tumors that produce vascular endothelial growth factors (VEGF) that hyperpermeabilize the tumor-associated neovasculatures and cause the leakage of circulating macromolecules and small particles; and (b) tumors lack an effective lymphatic drainage system, which leads to subsequent macromolecule or nanoparticle accumulation.

One aspect, therefore, of the disclosure encompasses surface-enhanced Raman spectroscopic active composite nanostructures comprising a core metallic, advantageously gold, nanoparticle, a Raman reporter molecule disposed on the surface of the core, and an encapsulating protective layer disposed on the surface of the core and the reporter molecule, wherein the encapsulated reporter molecule has a measurable surface-enhanced Raman spectroscopic signature.

In embodiments of the disclosure, the Raman reporter molecule may be selected from an isothiocyanate dye, a multi-sulfur organic dye, a multi-heterosulfur organic dye, a benzotriazole dye, or combinations thereof.

In embodiments of the disclosure, the reporter molecule is selected from a thiacyanine dye, a dithiacyanine dye, a thiacarbocyanine dye, or a dithiacarbocyanine dye. In other embodiments, the reporter molecule is selected from malachite green isothiocyanate, tetramethylrhodamine-5-isothiocyante, X-rhodamine-5-isothiocyanate, X-rhodamine-6-isothiocyanate, or 3,3'-diethylthiadicarbocyanine iodide.

In one embodiment of the disclosure, the core is gold, and may have a diameter less than about 200 nanometers.

In the embodiments of the nanostructures of the disclosure, the encapsulating material is a thiol-polyethylene glycol.

In other embodiments of the disclosure the nanostructures may further comprise a target-specific probe selectively binding a target on a cell.

In these embodiments, the target-specific probe may be selected from the group consisting of an antibody, a polypeptide, a polynucleotide, a drug molecule, an inhibitor compound, and a combination thereof, and wherein the targeting probe has an affinity for a marker on the surface of a target cell.

In one embodiment, the target-specific probe is an immunoglobulin, or a fragment thereof and in the embodiments of the disclosure the probe may be disposed on the hydrophobic protection structure. In one embodiment, the probe is a tumor-targeting ligand.

Another aspect of the disclosure encompasses methods of preparing a nanostructure according to the disclosure, comprising providing a gold nanoparticle, introducing the gold nanoparticle to a Raman reporter, whereupon the Raman reporter is disposed on the surface of the nanoparticle to form a nanoparticle-reporter complex, and disposing a protection structure layer on the surface of the nanoparticle-reporter complex, wherein the reporter molecule has a measurable surface-enhanced Raman spectroscopic signature.

In one embodiment of this aspect of the invention, the methods may further comprise depositing a cell target-specific probe to the protection structure layer, wherein the probe is selected from an antibody, a polypeptide, a polynucleotide, a drug molecule, an inhibitor compound, or a combination thereof.

In one embodiment of the method of this aspect of the disclosure, the core metallic nanoparticles are a colloid. In an advantageous embodiment, the core metallic nanoparticles is gold.

In embodiments of this aspect of the disclosure, the Raman reporter molecule may be selected from an isothiocyanate dye, a multi-sulfur organic dye, a multi-heterosulfur organic dye, a benzotriazole dye, or combinations thereof. In other embodiments of the disclosure, the reporter molecule is selected from a thiacyanine dye, a dithiacyanine dye, a thiacarbocyanine dye, or a dithiacarbocyanine dye. In yet other embodiments of this method of the disclosure, reporter molecule is selected from malachite green isothiocyanate, tetramethylrhodamine-5-isothiocyante, X-rhodamine-5-isothiocyanate, X-rhodamine-6-isothiocyanate, or 3,3'-diethyl-thiadicarbocyanine iodide.

In one embodiment of the disclosure, the encapsulating material is a thiol-polyethylene glycol.

Yet another aspect of the disclosure encompasses methods of imaging a biological sample, comprising delivering at least one nanostructure to a cultured cell or to an animal or human subject, wherein the nanostructure comprises a core gold nanoparticle, a Raman reporter molecule disposed on the surface of the core, and an encapsulating protective layer disposed over the core and the reporter molecule, and wherein the encapsulated reporter molecule has a measurable surface-enhanced Raman spectroscopic signature, allowing the nanostructure to contact a targeted biological cell or tissue, exciting the reporter molecule with a source of radiation, and measuring the surface enhanced Raman spectroscopy spectrum of the nanostructure corresponding to the reporter molecule, thereby detecting the presence of the nanostructure in the targeted cell or tissue.

In one embodiment of this aspect of the disclosure, the nanostructure may further comprise a target-specific probe, wherein the targeting probe selectively binds the nanoparticle to a targeted cell, thereby allowing detection of the targeted cell.

In another embodiment of the disclosure, the target cell is in a tissue of an animal or human subject.

In the embodiments of this aspect of the disclosure, the target cell may be a cancerous cell of an animal or human subject and the target-specific probe may selected from the group consisting of an antibody, a polypeptide, a polynucleotide, a drug molecule, an inhibitor compound, and a combination thereof, and wherein the targeting probe has an affinity for a marker on the surface of a target cell.

In one embodiment of the disclosure, the target-specific probe is a tumor-targeting ligand.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Reagents

Ultrapure water (18 MΩ cm$^{-1}$) was used throughout the work. The following chemicals were obtained from commercial sources and were used without further purification: 60-nm citrate-stabilized gold particles at a concentration of 2.6×1010 particles per milliliter (Ted Pella Inc.), near-infrared-emitting quantum dots (QD705, Invitrogen), malachite green isothiocyanate (MGITC) (Invitrogen), diethyl-thiatricarbocyanine iodide (DTTC) (Exciton), mPEG-SH (MW approximately 5 kDa) (Nektar Therapeutics), HS-PEG-COOH (MW approximately 3 kDa) (Rapp Polymers). The human carcinoma cells line Tu686 was established from a primary tumor in base of tongue. Human carcinoma cell line NCI-H520 was purchased from the American Type Culture Collection (ATCC). Cell culture media, fetal bovine serum, hemocytometer, and cell culture supplies were purchased from Fisher Scientific. All other reagents were obtained from Sigma-Aldrich at the highest purity available.

Example 2

Synthesis

Gold colloids with a target diameter of about 60 nm were synthesized according to literature procedures. All glassware was cleaned rigorously and rinsed with water prior to use. In a 50 mL glass flask, 30 mL of a 0.01% aqueous solution of $HAuCl_4$ was brought to a boil under magnetic stirring. Upon boiling, 180 μL of 1% sodium citrate was rapidly injected. Within minutes, the pale yellow solution turned deep purple and quickly progressed to red. The colloid was boiled for approximately 15 minutes to ensure complete reduction, was allowed to cool to room temperature, and was reconstituted to 30 mL before use.

To prepare SERS active composite nanostructures with an embedded Raman reporter (i.e., a reporter molecule), about 0.1 g mixed bed ion-exchange resin was stirred with the freshly prepared gold colloid to remove excess ions. The resin was removed either by filtration or careful decanting, and the colloid was diluted with an equal amount of water. A Raman reporter was added under rapid stirring to a concentration not exceeding about $7.5 \times 10^{-8}$ M and was allowed to equilibrate for about 15 minutes.

Measurements

A scanning spectrophotometer (Shimadzu, Columbia, Md.) was used to acquire UV-visible absorption spectra. High-magnification transmission electron micrographs were taken using a Phillips CM200 electron microscope and were recorded on a TVIPS 2 k by 2 k CCD. Bulk Raman spectra were recorded using a dispersive Raman spectroscopy system (Solution 633, Detection Limit, Laramie, Wyo.). Single-particle spectra were obtained with an inverted optical microscope (Diaphot 200, Nikon, Melville, N.Y.), equipped with a mixed gas argon/krypton ion laser (Lexel 3500, Fremont, Calif.) for 647 nm excitation.

Regions of interest were first screened with wide-field illumination, and Raman-active particles were located with a video-rate intensified CCD (ICCD, PTI, Inc., Lawrenceville, N.J.) mounted to the front microscope port. Confocal optics was then used to focus on an individual SERS active composite nanostructures, and back-scattered Raman signals were collected through a microscope objective (Plan 100x, oil immersion, NA=1.25). A triple-bandpass filter (Chroma Tech, Brattleboro, Vt.) was used to block the laser line and extraneous signals. Spectroscopic signatures were obtained with a CCD detector (TKB512, Princeton Instruments, Trenton, N.J.) mounted on a single-stage spectrometer (Model 270M, Spex, Edison, N.J.).

Example 3

Preparation of Pegylated SERS Nanoparticles

A freshly prepared reporter solution (3-4 μM) was added dropwise to a rapidly mixing gold colloid at a 1:6 reporter solution/colloid volume ratio, which facilitated even distributions of the reporter molecules on the gold particle surface. The molar ratio of reporter molecules to gold particles was optimized for maximal SERS intensities and minimal colloid aggregation. For example, the optimized surface coverage values were 14,000 malachite green isothiocyanate molecules per 60 nm gold particle, and about 15,300 crystal violet molecules per gold particle of the same size. It should be noted that the above parameters (that is, stock reporter concentration, volume ratio of stock reporter solution to gold nanoparticle solution, and the rate of reporter addition to gold) all affected the aggregation state of the resulting tags. When reporter solution was added to gold colloid, we observed higher SERS signals than when adding gold to reporter.

After 10 mins, a thiol-PEG solution (10 μM) was added dropwise to the Raman-encoded colloids, with a minimum ratio of 30,000 PEG-SH molecules per 60-nm gold particle. This surface coverage corresponded to a complete PEG monolayer on the gold particle surface, and was necessary to stabilize gold colloids against aggregation under various conditions. Simple geometric calculations showed that each thiol-PEG molecule occupied a footprint area of 0.35 $nm^2$ on the gold surface, consistent with the literature data reported for PEG-SH in a brush conformation. Importantly, addition of 10- to 20-fold excess PEG-SH did not result in any changes in colloid stability or in the thickness of the polymer coating layer.

Example 4

Nanoparticle Characterization

UV-Vis absorption spectra were recorded on a Shimadzu (UV-2401) spectrometer using disposable polyacrylic cuvettes. Transmission electron micrographs (TEM) were taken by using a Hitachi H7500 high-magnification electron microscope. The nanoparticle sample (5 μl) was dropped onto copper 200-mesh grids that were pretreated with UV light to reduce static electricity. After 30 min, the solvent was drained with a filter paper and a phosphotungstic acid stain solution (1% by weight, adjusted to pH 6) was applied for 30 secs Fresh tumor tissue specimens were fixed in 0.1 M cacodylate buffer (pH 7.4) containing 2.5% glutaraldehyde at 4° C. The tissue was rinsed three times in 0.1 M cacodylate buffer for 15 min, post-fixed with 1% $OsO_4$ buffer, and then dehydrated and embedded in a resin (Epon). Ultrathin sections (approximately 60 nm) were produced with an ultratome machine, and were placed on copper grids for TEM imaging.

DLS data were obtained by using a Brookhaven 90Plus particle size analyzer instrument. Each sample was measured three times consecutively. SERS spectra were recorded on a compact Raman system using 633 nm (3 mW) or 785 nm (40 mW) excitation (Advantage Raman Series, DeltaNu). In vivo SERS spectra were collected using 785-nm laser excitation on a handheld Raman system (Inspector Series, DeltaNu). The laser beam diameter was 35 μm at the focal point, so the probe volume was estimated to be about 23 nl at 633 nm excitation and about 19 nl at 785 nm excitation. SERS intensities were normalized to the Raman spectra of cyclohexane and polystyrene to correct for variations in optical alignment and instrument response. The spectral resolution was about 5 cm-1 for both the Advantage and the Inspector Raman systems.

For imaging of single SERS nanoparticles and quantum dots, a narrow bandwidth laser excitation filter (633±3 nm) and a long-pass emission filter (655LP, Chroma Tech) were employed with an Olympus IX71 inverted microscope. The images were taken with 750 ms exposure time and were the average of 50 images by using an electron-multiplying (EM) CCD camera (Hamamatsu, Model C9100-12) attached to the microscope. The use of long exposure times and image averaging cancelled out any signal fluctuations of single nanoparticles. For quantitative comparison of SERS and quantum dot signal intensities, the wavelength dependence factor was corrected by using the CCD camera response curve.

Example 5

Conjugation with scFv Ligands scFv B10, an antibody fragment specific for human EGFR, was isolated from the YUAN-FCCC human naive phage display library by using established solid phase biopanning methods. Large quantities of scFv were purified from bacterial extracts under native conditions using a $Ni^{2+}$ NTA-agarose column (Qiagen). Protein purity greater than 95% was determined by using sodium dodecyl sulfate (SDS)-PAGE. The heterofunctional linker HS-PEG-COOH (430 □l and 1 □M) was added dropwise to 2.2 ml Au-MGITC (or Au-DTTCI) solution in a polypropylene tube under rapid mixing. The number of carboxy groups per gold particle was controlled to be approximately 5,000 by changing the amount of linker molecules used. After 15 min of mixing, the gold nanoparticles were exposed to a large volume of PEG-SH (1.6 ml at 10 □M) to fill the areas not covered by the heterofunctional PEG, yielding well-shielded and stable particle surfaces. Before covalent ligand conjugation at the carboxylic acid functional groups, the gold particles were purified by three rounds of centrifugation (1,000 g) and resuspension in PBS.

To activate the —COOH groups on the particle surface for covalent conjugation, freshly prepared ethyl dimethylaminopropyl carbodiimide (EDC) solution (5 □l) at a concentration of 40 mg/ml) and sulfo-NHS (5 □l at 110 mg/ml) were mixed vigorously at 25° C. for 15 min. Excess EDC and sulfo-NHS were separated from the activated nanoparticles by three rounds of centrifugation (1,000 g) and resuspension in PBS using Nanosep 10K MWCO OMEGA membrane (Pall Life Sciences). The purified gold particles with activated carboxyl groups were then reacted with the scFv antibody (11.2 nmol) at 25° C. for 2 h, and the reaction mixture was stored at 4° C. for overnight. Excess scFv ligand was removed by three rounds of centrifugation and resuspension in PBS using 100K MWCO OMEGA membranes. Based on protein absorption measurement at 280 nm, we estimated that there were about 600 scFv molecules per gold particle. This value was further confirmed by using a fluorescently labeled scFv ligand to determine the conjugation ratio at higher sensitivity. The fully functionalized nanoparticles were characterized by UV-Vis, TEM and DLS, and their colloidal stability and optical properties were essentially the same as that of control nanoparticle tags.

Example 6

Cellular SERS Studies

Tu686 and H520 cells were cultured in DMEM/Ham's F-12 (1:1) and RPMI-1640 supplemented with 10% heat-inactivated fetal bovine serum and antibiotics (streptomycin, penicillin G and amphotericin B), respectively, and were maintained in a humidified incubator at 37° C., 5% $CO^2$. The cells were grown to confluence in 35-mm dishes. Cell staining procedures were performed under sterile conditions on a tabletop binding incubator at 25° C. Live cells were gently mixed with the scFv-conjugated SERS nanoparticles (15 pM in PBS) for 30 min, and then were harvested by gentle scraping. The cells were subjected to four rounds of washing with ice-cold PBS, and were resuspended in 500 □l PBS before SERS measurement. A portion of the cells were incubated with pegylated control SERS tags to assess nonspecific binding and internalization. An additional portion of the cells received neither control SERS tags nor EGFR-SERS tags, and were used as controls to assess background cell scattering. SERS spectra were normalized to cell numbers as determined with a Coulter counter.

For quantitative comparison, we subtracted the pure cell scattering spectra to generate difference spectra in FIG. 3. All spectra were taken in cell suspensions. Based on a cell density of $1\times10^6$ cells per ml, we estimated that the laser detection volume contained approximately 20 to 30 labeled cells. We did not observe changes in either spectral signatures or intensities upon repeated examination of the unfixed cell samples over a period of 3 days or upon cell fixation in formaldehyde solution. These cell-suspension measurements avoided the problems of nanoparticle tagging and cellular heterogeneities and were found to be highly reproducible.

Example 7

Tumor Xenografts and In Vivo SERS

A healthy nude mouse received 50 femtomoles of pegylated SERS nanoparticles administered at two locations: (i) subcutaneous injection (1-2 mm under skin); and (ii) deep muscular injection (1 cm under the skin). Different locations were examined by using an NIR Raman spectrometer (Inspector Series, DeltaNu). The subcutaneous SERS spectrum was obtained in 3 secs, the muscular spectrum in 21 secs, and the control spectrum (obtained in an area away from the injection site) also in 21 secs.

Figure 10:
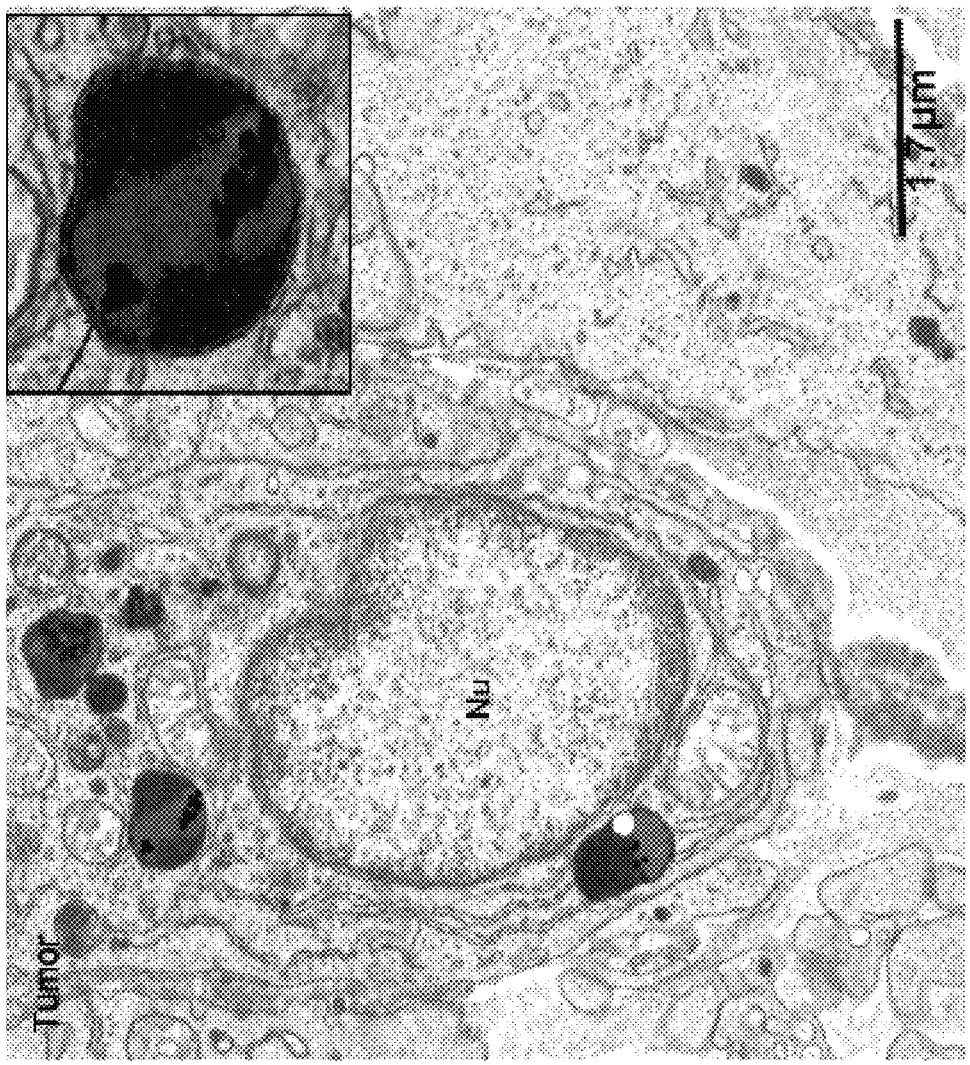
FIG. 10 illustrates transmission electron micrographs showing tumor uptake of EGFR-targeted gold nanoparticles, their clustering and localization in intracellular organelles such as endosomes. The inset is an expanded view of gold nanoparticles in an organelle. Nu refers to cell nucleus.
Figure 11:
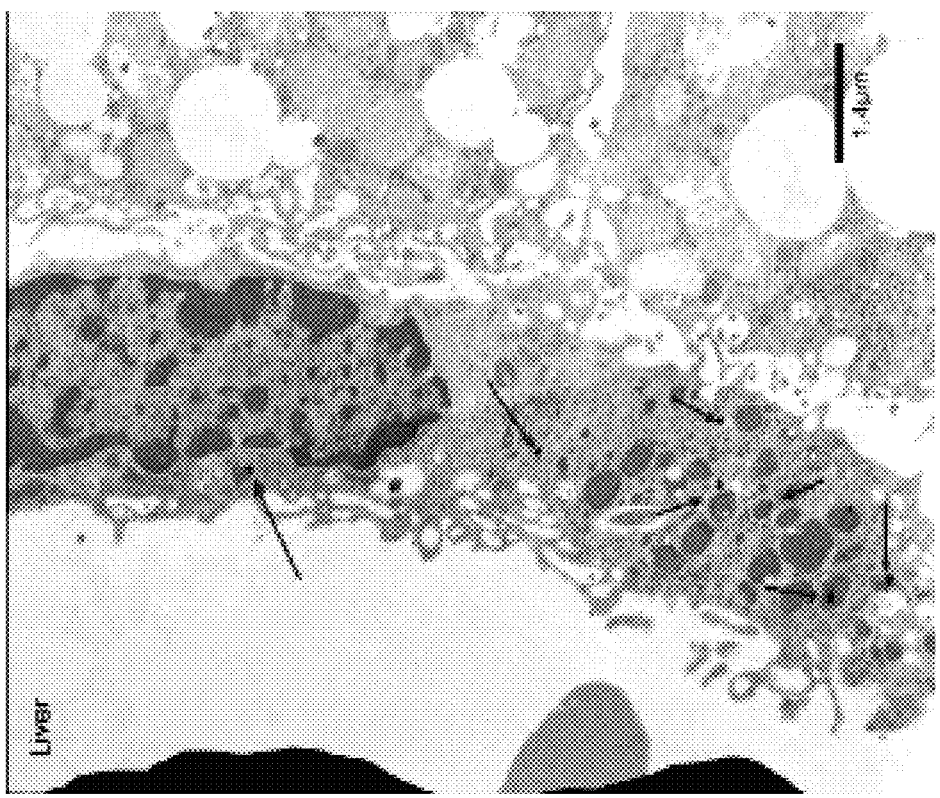
FIG. 11 illustrates transmission electron micrographs showing nonspecific uptake of gold nanoparticles by liver Kuffper cells showing primarily single gold nanoparticles localized in early- and late-stage endosomes (indicated by arrows).

Tu686 cells ($5\times10^6$) were injected subcutaneously into the back flank area of approximately 6- to 8-week-old female nude mice (NC rathymic, nu/nu). The mice were divided into two groups for passive and active targeting studies. When the tumor size reached 3 mm diameter, the nude mice received 45 femtomoles of scFv EGFR-conjugated SERS tags and pegylated control SERS tags, respectively, by tail vein injection. After 5 hrs, the mice were placed under anesthesia by injection of 70 □l of ketamine and xylazine mixture solution and were examined by using a Raman spectrometer with 20 mW laser power at 785 nm. The laser beam was focused to the tumor or the liver anatomical region for both the targeted and nontargeted SERS nanoparticles. With a focal length of approximately 9 mm, SERS spectra were obtained in a completely noncontact and non-invasive manner. Results are shown in FIGS. 5A-5C. After spectroscopic data acquisition, the mice were killed to collect major organs for ICP-MS biodistribution analysis. A small portion of each fresh tissue sample was also fixed immediately in 0.1 M cacodylate buffer to prepare TEM thin sections (FIGS. 10 and 11).

Briefly, major organ tissues were rinsed with ethanol three times and then lyophilized and weighed into clean vials for acid digestion. After 2 days of strong acid digestion, the samples were purified and diluted 35-fold for analysis by ICP-MS (inductively coupled plasma-mass spectrometry). The experiments were carried out in five independent runs for statistical analysis. Each run had two mice with freshly prepared SERS tags, one with active targeting and the other with passive targeting. One group of the animals was used for longer term toxicity studies.

Example 8

Design and Characterization of Pegylated SERS Nanotags

Figure 1D:
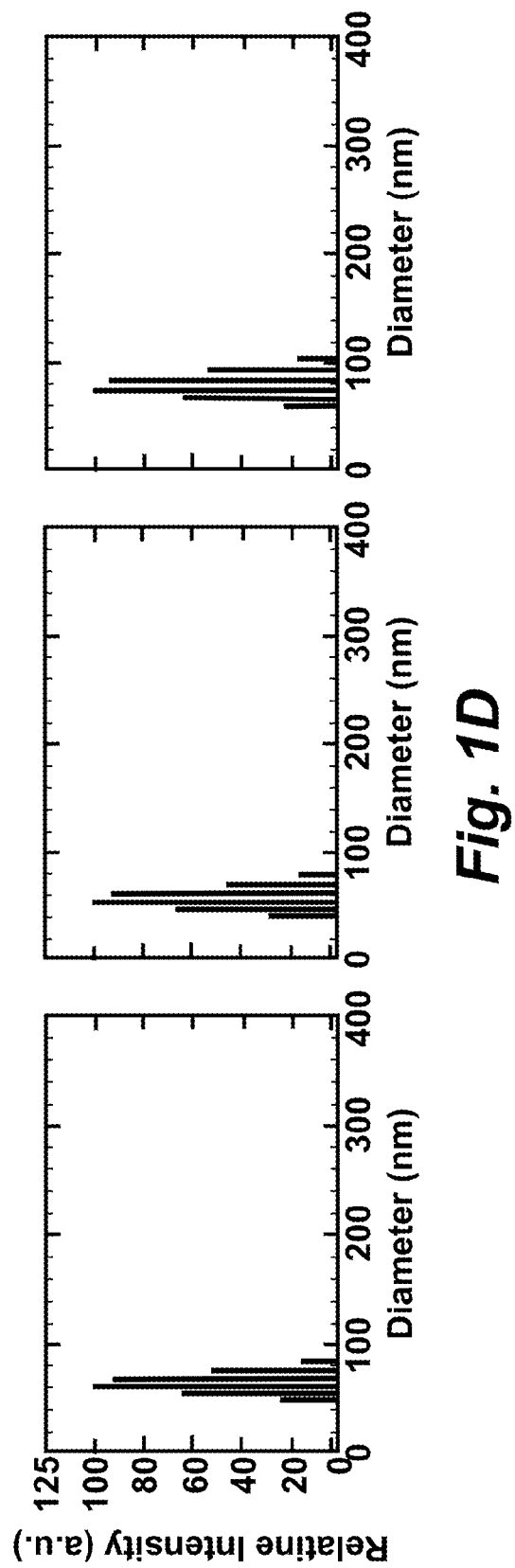
FIG. 1D illustrates the dynamic light scattering size data obtained from the original, Raman-encoded, and PEG-stabilized gold nanoparticles shown in FIG. 1A.

FIGS. 1A-1D show the design and preparation of pegylated gold nanoparticles with embedded spectroscopic tags and their schematic structures. Also shown are their optical absorption spectra (FIG. 1B), transmission electron microscopy (TEM) structures (FIG. 1C), and hydrodynamic size data (FIG. 1D). The original gold particles (60-nm diameter) were encoded with a Raman reporter and stabilized with a layer of thiol-PEG. Previous experimentation had shown that gold nanoparticles with a core size of approximately 60-80 nm were most efficient for SERS at red (630-650 nm) and near-infrared (785 nm) excitations (Krug et al., (1999) J. Am. Chem. Soc. 121: 9208-9214).

This spectral region is known as a 'clear window' for optical imaging because the hemoglobin (blood) and water absorption spectra are minimal. Beyond the SERS effect, we also achieved resonance Raman enhancement by using reporter molecules with electronic transitions at 633 nm or 785 nm. The gold plasmonic resonance spectra remained essentially unchanged (<1-nm red shifts), even when the gold particles were coated with a large number of molecules (about $1.4$-$1.5 \times 10^4$) and stabilized with a layer of PEG molecules (FIG. 1B). We note that single-molecule SERS occurs only at special active sites or junctions, and it is not required for tumor detection. In fact, with a large number of reporter molecules adsorbed on the particle surface, the achieved total signal intensities exceeded that of single-molecule SERS. The PEG coating was clearly observed as a thin white layer of approximately 5 nm by TEM negative staining, whereas the particle's 'wet' hydrodynamic diameter increased by 20 nm after pegylation, as measured by hydrodynamic light scattering (DLS) in buffered saline. At a core particle size of 60 nm, a minimum of 30,000 thiol-PEG molecules (MW=5 kDa) per gold nanoparticle was necessary to achieve complete protection against salt-induced colloid aggregation. This surface coverage corresponded to a footprint area of approximately 0.35 nm$^2$ per PEG molecule, in agreement with that reported by another group for thiol-PEG adsorbed on colloidal gold in a brush conformation. After this shielding layer was completed, the use of additional thiol-PEG up to 10- to 20-fold excess had little effect on the coating thickness, as measured by both TEM and DLS.

Example 9

The stability of pegylated gold nanoparticles was studied by measuring their SERS signals (both frequency and intensity) under a wide range of conditions including concentrated salts (1-2 M), strong acids (0.1 M HCl), strong bases (1 M NaOH) and organic solvents (methanol, ethanol and dimethyl sulfoxide or DMSO) FIGS. A and B. In the absence of PEG protection, the gold nanoparticles rapidly 'crash' (that is, aggregate and precipitate) under these harsh conditions. With PEG protection, the gold particles and their SERS spectra are completely stable, with only minor relative intensity changes at pH 1-2 (due to protonation and relative orientation changes of the reporter molecule on the gold surface).

The observation of intense SERS signals with a thiol-PEG coating is counterintuitive because the reporter molecules on the particle surface are expected to be displaced by thiol compounds (which are known to spontaneously form a monolayer on gold). Also surprising is that a range of Raman reporters such as crystal violet, Nile blue, basic fuchsin and cresyl violet were not displaced by thiol-PEG, even without an anchoring isothiocyanate (—N=C=S) group. In fact, the SERS signals of crystal violet and other dyes were strongly protected by thiol-PEG, and were stable for >11 months at 25° C. A common feature for these reporter dyes is that they are positively charged and contain delocalized pi-electrons. In contrast, organic dyes with negative charges such as sodium fluorescein gave only weak and unstable SERS signals on the citrate-stabilized gold particles (also negatively charged) used in this work. Thus, we believe that both electrostatic interactions and delocalized pi-electrons are important for strong dye adsorption, likely at gold surface sites that do not compete with thiol-PEG adsorption. It is also possible that the thiol-PEG layer protected and stabilized the adsorbed reporter dyes by steric shielding and electronic interactions.

For cellular and in vivo imaging applications, we compared the excitation and emission spectral properties of pegylated gold nanoparticles and near-infrared quantum dots. The gold nanoparticles provided much richer spectroscopic information, and their emission peaks (full width at half maximum FWHM=1-2 nm) were 20-30 times narrower than those of quantum dots (FWHM=40-60 nm) (FIGS. 2A and 2B). Under identical experimental conditions, the pegylated gold particles were >200 times brighter (on a particle-to-particle basis) than near-infrared-emitting quantum dots in the spectral range of 650-750 nm (see single particle images in FIGS. 2C and 2D, and statistical data in FIGS. 2E and 2F). The pegylated gold nanoparticles had hydrodynamic sizes of about 80 nm (diameter) and were completely nontoxic to cultured cells when tested over 3-6 days. In the absence of surface-enhanced Raman signals, near-infrared gold nanoshells have recently been used as a contrast enhancement agent for optical coherence tomography as well as for photothermal tumor ablation, but this approach does not provide molecular signatures for spectral encoding or multiplexing.

Example 10

Spectroscopic Detection of Cancer Cells

Figure 3A:
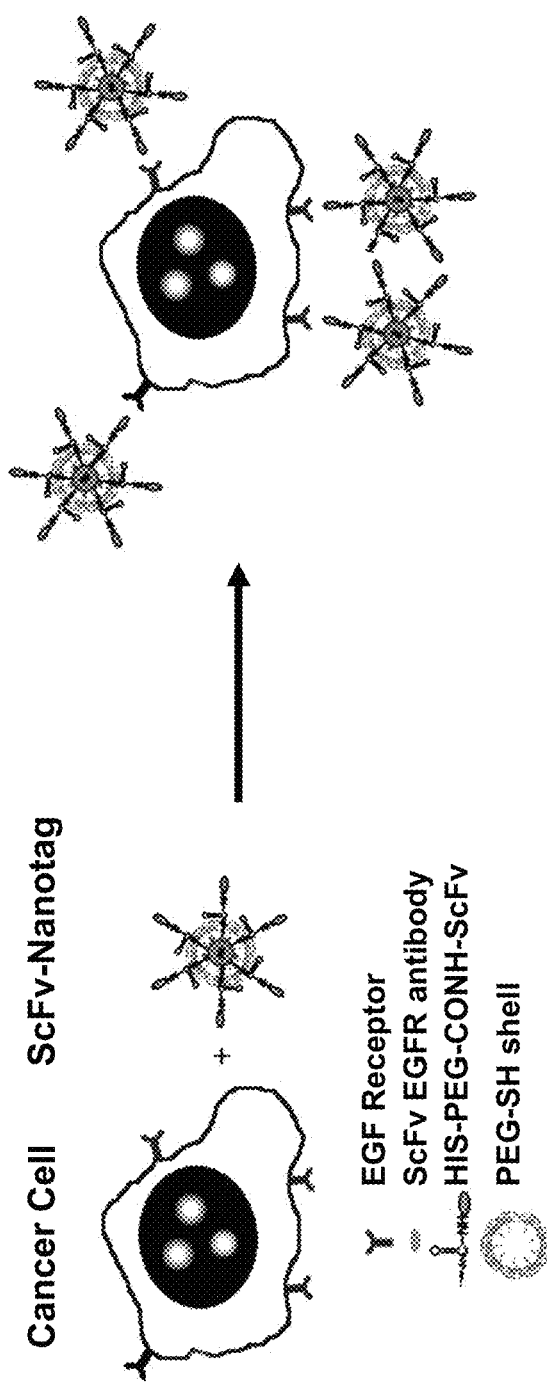
FIGS. 3A and 3B illustrate cancer cell targeting and spectroscopic detection by using antibody-conjugated SERS nanoparticles.
Figure 3B:
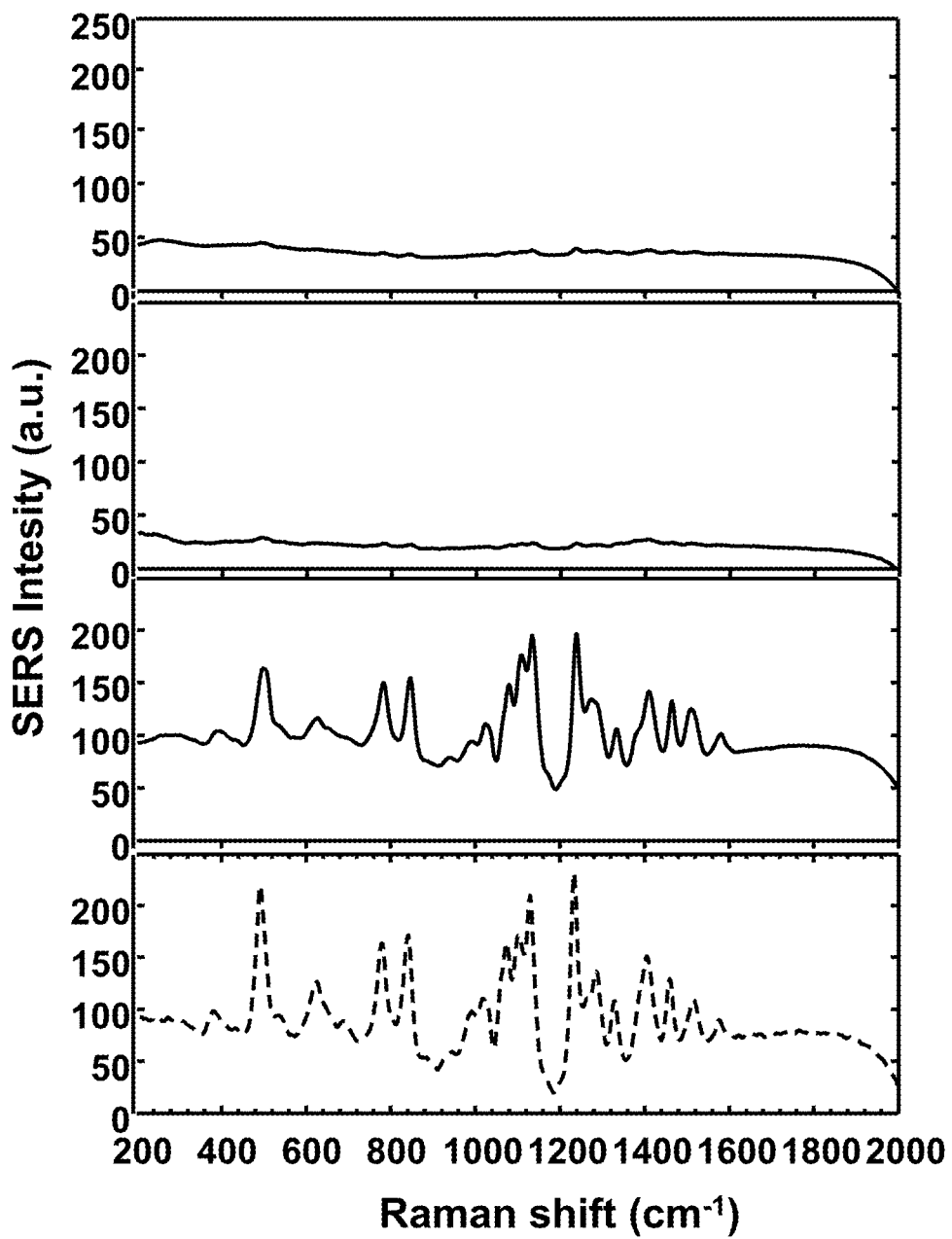
Figure 8:
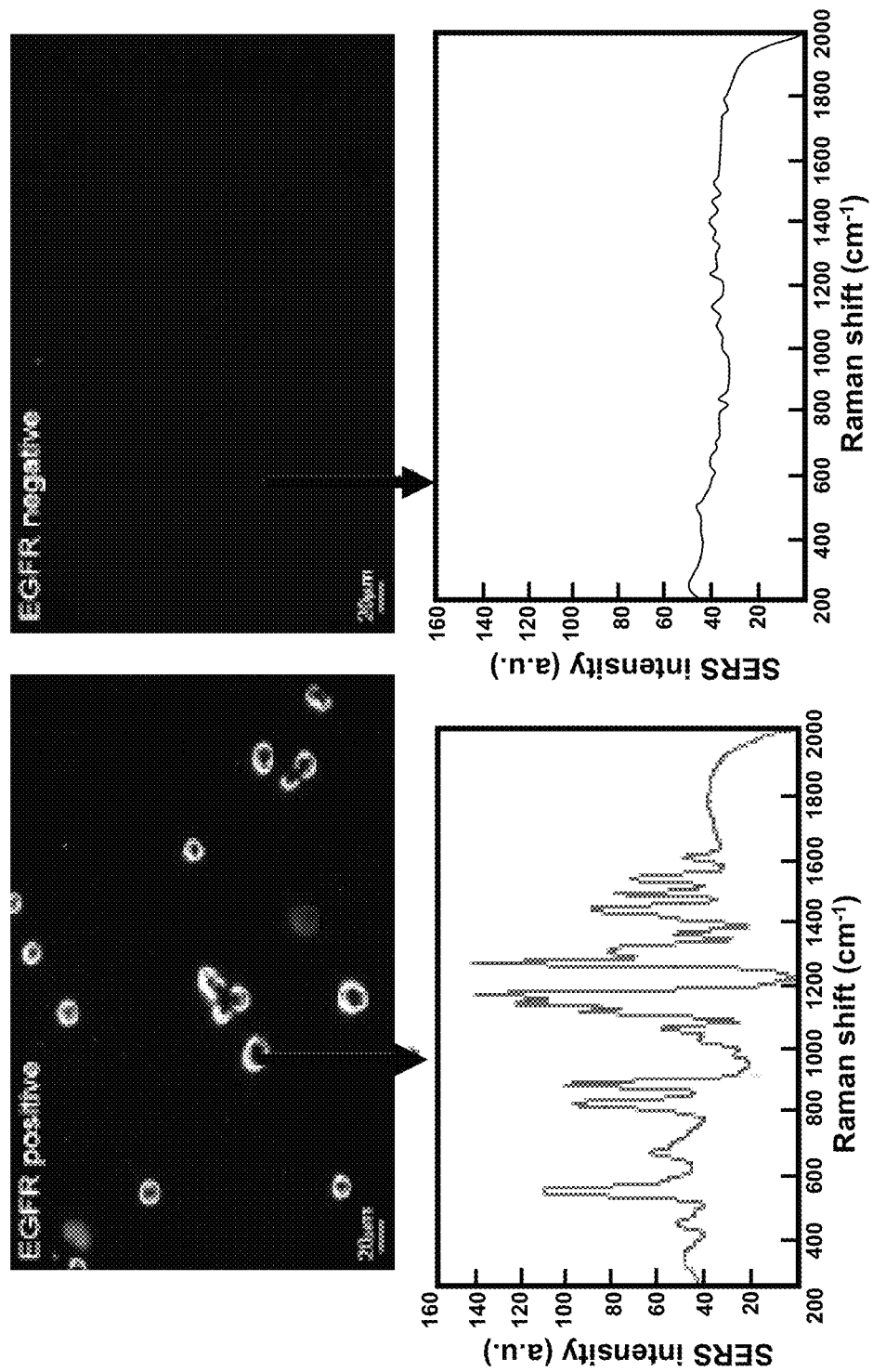
FIG. 8 illustrates SERS spectra and correlated surface plasmon imaging of single cancer cells. Upper panels: Reflective mode dark-field images of live Tu686 cells (EGFR positive) and H520 6 cells (EGFR negative) tagged with scFv-conjugated gold nanoparticles. The images were acquired with Olympus Q-Color 5 CCD camera at an exposure time of 250 milliseconds. Lower panels: SERS spectra obtained from single cells as indicated by arrows. The Raman reporter dye was diethylthiatricarbocyanine (DTTC).

For cancer cell detection, targeted gold nanoparticles were prepared by using a mixture of thiol-PEG (about 85%) and a heterofunctional PEG (SH-PEG-COOH) (about 15%). The heterofunctional PEG was covalently conjugated to an scFv antibody (MW=25 kDa), a ligand that binds to the EGFR with high specificity and affinity as schematically shown in FIG. 3A. UV-Vis absorption and fluorescence data indicated that about 600 copies of the scFv ligand were conjugated to each gold nanoparticle. FIG. 3B shows cellular binding and SERS spectra obtained by incubating the scFv-conjugated gold nanoparticles with human carcinoma cells. The human head-and-neck carcinoma cells (Tu686) were EGFR positive ($10^4$-$10^5$ receptors per cell), and were detected by strong SERS signals. In contrast, the human non-small cell lung carcinoma (NCI-H520) did not express EGFR, showing little or no SERS signals. To confirm targeting specificity, we preincubated Tu686 cancer cells in a tenfold excess of free scFv EGFR antibody, and then added EGFR-labeled SERS nanoparticles for competitive binding studies. After three rounds of washing, the cells showed only negligible SERS signals. Also tested and confirmed were the binding specificity of SERS nanoparticles conjugated to secondary antibodies in a two-site sandwich format. For control cancer cells (EGFR negative) and control nanoparticles (plain PEG-coated nanotags and PEG-nanotags functionalized with a nonspecific IgG antibody), the spectra showed a weak but reproducible background as shown in FIG. 3B. The low background was probably caused by residual SERS nanoparticles in the mixing solution that were not completely removed during cell isolation, but there could also have been contributions from nonspecific binding or nanoparticle internalization. An infrared dye (diethylthiatricarbocyanine or DTTC) was used as a spectroscopic reporter, and achieved surface-enhanced resonance Raman scattering (SERRS) at 785-nm excitation. This resonance condition did not lead to photobleaching because the adsorbed dyes were protected from photo-degradation by efficient energy transfer to the metal particle. The resonance effect can further increase the surface-enhanced Raman signals by 10- to 100-fold, sensitive enough for Raman molecular profiling studies of single cancer cells (FIG. 8). This sensitivity is important for investigating the heterogeneous nature of cancer tissue specimens removed by surgery, and circulating tumor cells captured from peripheral blood samples. Single-cell profiling studies are of great clinical significance because EGFR is a validated protein target for monoclonal antibody and protein-kinase-based therapies.

Example 11

In Vivo Tumor Targeting and Detection

Figure 4:
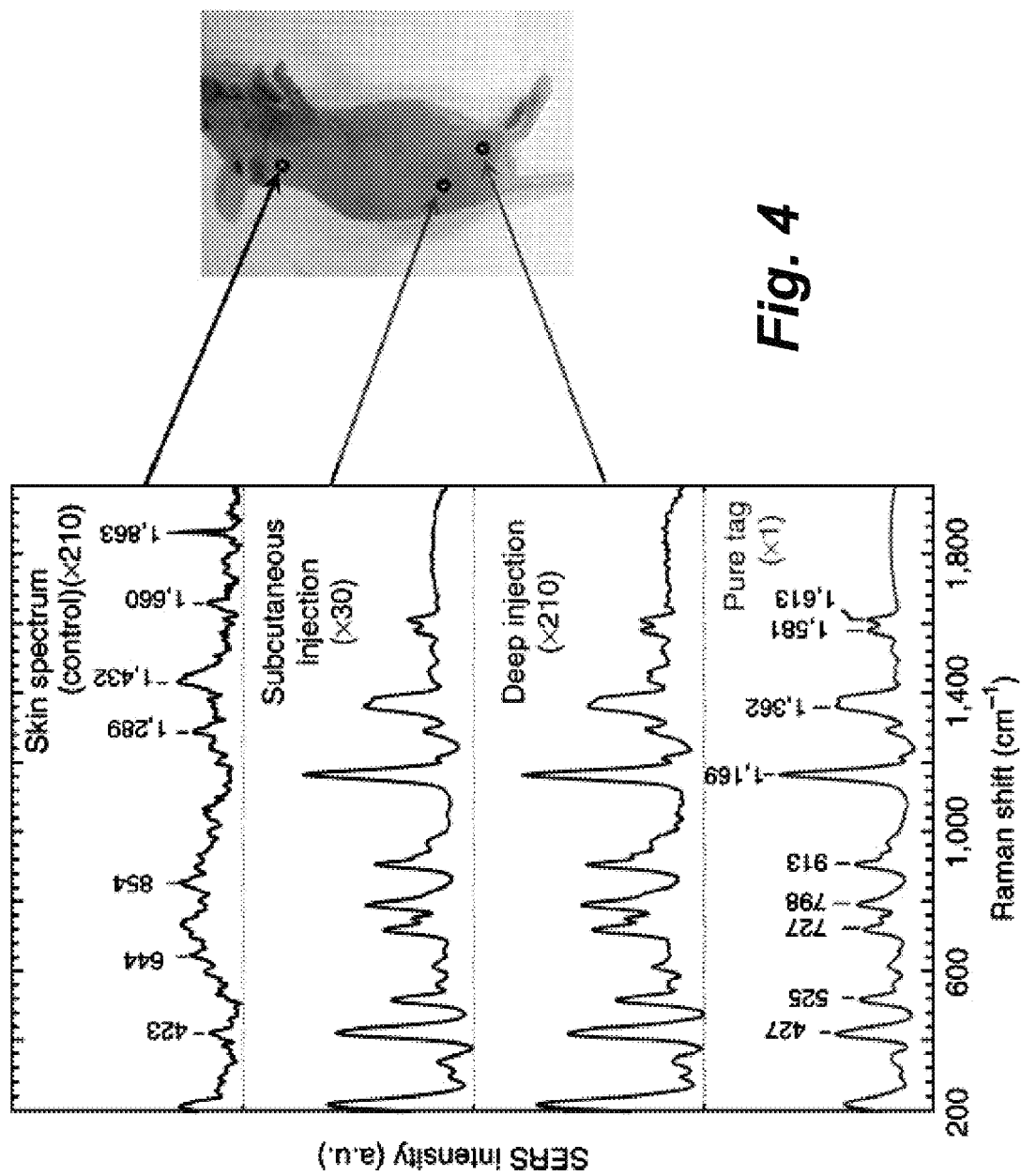
FIG. 4 illustrates in vivo SERS spectra obtained from pegylated gold nanoparticles injected into subcutaneous and deep muscular sites in live animals. The injection sites and laser beam positions are indicated by circles on the animal.

A major challenge for in vivo optical imaging and spectroscopy is the limited penetration depth, due to light scattering and absorption in animal tissues. To determine whether SERS spectra can be acquired from pegylated gold nanoparticles buried in animal tissues, we injected small dosages of nanoparticles into subcutaneous and deep muscular sites in live animals. Highly resolved SERS signals were obtained from subcutaneous as well as muscular injections as shown in FIG. 4.

A healthy nude mouse received 50 □l of the SERS nanoparticles tags (1 nM) by subcutaneous (1-2 mm under the skin) or muscular (approximately 1 cm under the skin) injection. The subcutaneous spectrum was obtained in 3 secs, the muscular spectrum in 21 sec, and the control spectrum (obtained in an area away from the injection site) also in 21 sec. The reference spectrum was obtained from the SERS nanoparticles in PBS solution in 0.1 secs The spectral intensities are adjusted for comparison by a factor (×1, ×30 or ×210) as indicated. The Raman reporter molecule is malachite green, with spectral signatures at 427, 525, 727, 798, 913, 1,169, 1,362, 1,581 and 1,613 cm-1. These features are distinct from the animal skin Raman signals (see the skin spectrum). Excitation wavelength, 785 nm; laser power, 20 mW.

The in vivo SERS spectra were identical to that obtained in vitro (saline solution), although the absolute intensities were attenuated by 1-2 orders of magnitude. Based on the high signal-to-noise ratios, we estimated that the achievable penetration depth was about 1-2 cm for in vivo SERS tumor detection (also confirmed by deep tissue injection studies).

For in vivo tumor targeting and spectroscopy, the gold nanoparticles conjugated with the scFv antibody were injected systemically (through tail veins) into nude mice bearing a human head-and-neck tumor (Tu686). FIGS. 5A and 5B shows SERS spectra obtained 5 hrs after nanoparticle injection by focusing a near-infrared, 785-nm laser beam on the tumor site or on other anatomical locations (e.g., the liver or a leg). Substantial differences were observed between the targeted and nontargeted nanoparticles in the tumor signal intensities, whereas the SERS signals from nonspecific liver uptake were similar. This result indicates that the scFv-conjugated gold nanoparticles were able to target EGFR-positive tumors in vivo. Time-dependent SERS data further indicate that nanoparticles were gradually accumulated in the tumor for 4-6 hrs, and that most of the accumulated particles stayed in the tumor for >24-48 hrs.

Example 12

In Vivo Nanoparticle Distribution and Intracellular Localization

Figure 6:
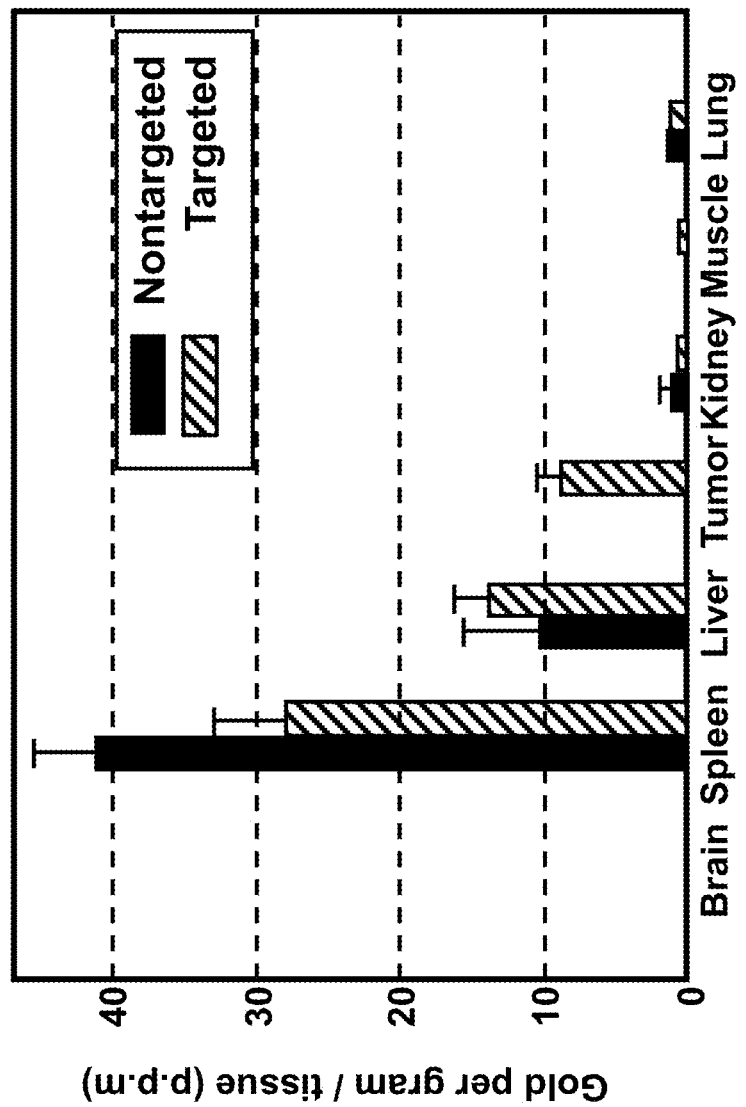
FIG. 6 illustrates biodistribution data of targeted and nontargeted gold nanoparticles in major organs at 5 hrs after injection as measured by inductively coupled plasma-mass spectrometry (ICP-MS). Note the difference in tumor accumulation between the targeted and nontargeted nanoparticles. The s.d. error bars were calculated based on four animals (n=4) in each study group.

Quantitative biodistribution studies using inductively coupled plasma-mass spectrometry (ICP-MS) revealed that the targeted gold nanoparticles were accumulated in the tumor 10 times more efficiently than the nontargeted particles as shown in FIG. 6. The ICP-MS data also confirmed nonspecific particle uptake by the liver and the spleen, but little or no accumulation in the brain, muscle or other major organs, similar to the biodistribution data reported for gold nanoshells injected into healthy mice31. Ultrastructural TEM studies further revealed that the SERS nanoparticles were taken up by the EGFR-positive tumor cells, and were localized in intracellular organelles such as endosomes and lysosomes as shown in FIGS. 10 and 11. The in vivo endocytosed nanoparticles had crystalline and faceted structures, in agreement with the finding that nearly identical SERS spectra were obtained from the encoded gold nanoparticles in vitro and in vivo. The pegylated gold particles appeared to be intact and stable in systemic circulation as well as after being taken up into intracellular organelles. No toxicity or other physiological complications were observed for the animals after 2-3 months of gold particle injection.

Example 13

Stability of Pegylated SERS Nanoparticles Under Harsh Conditions

Figure 7:
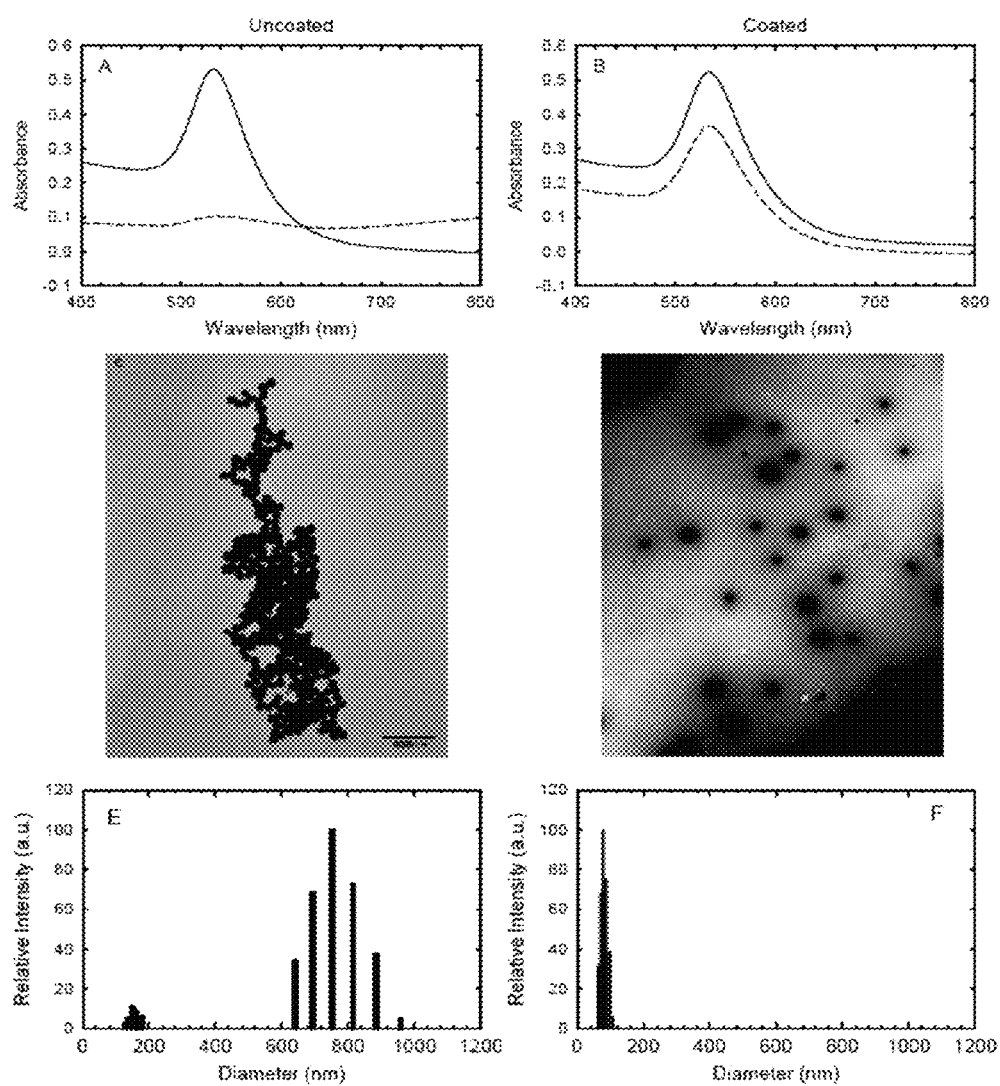
FIG. 7 illustrates a stability comparison of uncoated (left column) and PEG-SH coated (right column) Au-MGITC complexes. Top panels are UV-vis absorption spectra of uncoated (left) and coated (right) Au-MGITC in water (solid curves) and PBS (dashed curves); middle panels are TEM images of uncoated (left) and coated (right) Au-MGITC in PBS; bottom panels are the DLS size distributions of uncoated (left) and coated (right) Au-MGITC in PBS. MGITC is the abbreviation for malachite green isothiocyanate (ITC).

Four independent techniques verified the high degree of stability of Au-MGITC-PEG-SH in concentrated PBS solution. PEG-SH coated and uncoated Au-MGITC complexes were examined by UV-vis absorption spectroscopy, TEM, DLS, and visual observation, as shown in FIGS. 7A and 7B) PBS addition to uncoated Au-MGITC immediately aggregated and precipitated the colloid as evidenced by dramatic spectral changes in UV-vis absorption spectrum, large aggregates in TEM, and the appearance of a distinct population of particles of 600-1000 nm hydrodynamic diameter, and an obvious color change from pink to clear. In contrast, PEG-SH coated Au-MGITC treated with PBS showed a preservation of the characteristic plasmon resonance peak of 60 nm gold, a majority of single particles by TEM (with a small population of clusters due to solvent evaporation), a unimodal, narrow size distribution of particles in DLS, and the pink color. The effects of a wide range of conditions encountered in bioconjugation and cell labeling procedures were investigated for their effects on the spectral signatures of PEG-SH coated SERS tags.

Figure 18:
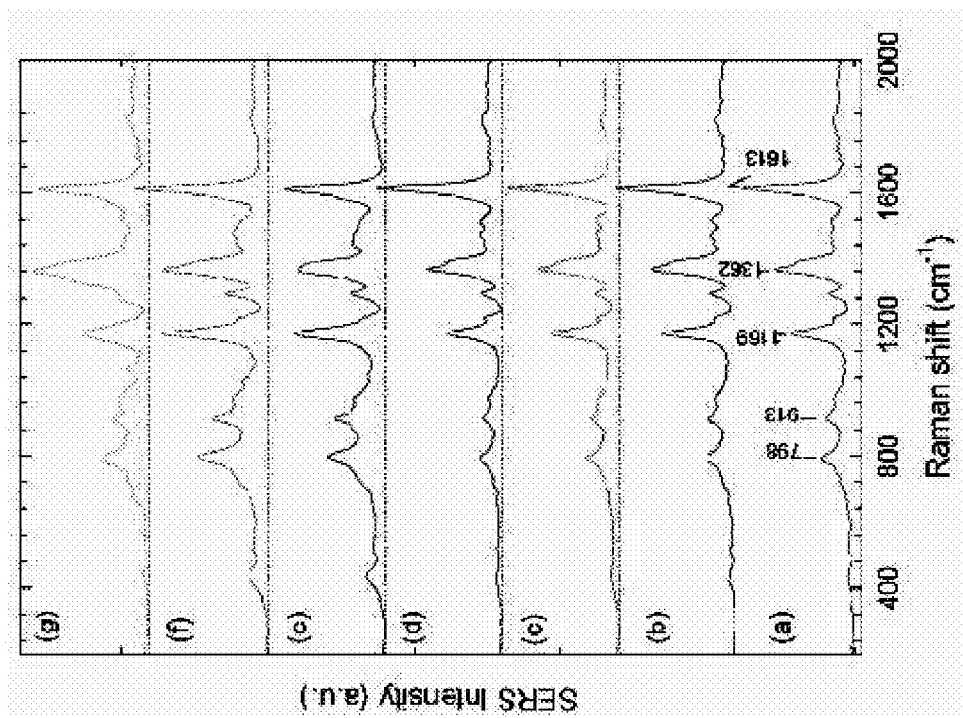
FIG. 18 illustrates SERS spectra of Au-MGITC-PEG-SH redispersed in (panel a) pure water, (panel b) 10×PBS, (panel c) pH 12 aqueous solution, (panel d) pH 2 aqueous solution, (panel e) ethanol, (panel f) methanol, (panel g) DMSO, then transferred back to water. The reporter dye is malachite green isothiocyanate (MGITC), with distinct spectral signatures as labeled. Excitation wavelength: 633 nm; laser power: 5 mW.

Au-MGITC-PEG-SH was pelleted by centrifugation, redispersed in new solvents, and examined by SERS spectroscopy. There was no significant spectral changes when Au-MGITC-PEG-SH was redispersed in 10-fold concentrated PBS (1.37 M NaCl), basic water (pH 12), acidic water (pH 2), ethanol, and methanol comparing with reference spectrum of Au-MGITC in water (FIG. 18). A slight change in relative peak intensities of the Raman bands at 1615, 1365, and 1172 cm-1 at pH 2 was noticed, possibly due to relative orientation changes of MGITC on the Au surface, but no shift in vibrational frequencies was observed within the instrument resolution of 5 cm-1.

Redispersion of Au-MGITC-PEG-SH in dimethylsulfoxide (DMSO) masked the spectral features of the reporter due to the strong Raman cross section of DMSO. Interestingly, the original MGITC spectral signature was recovered after the DMSO solvated tag was stored under ambient conditions for 60 days and then redispersed in water (FIG. 18, panel 'g'). Although uncoated Au-MGITC coalesced upon 5 centrifugations, PEG-SH coated SERS tags did not form aggregates under any of the above conditions tested.

Example 14

SERS Spectra and Correlated Plasmonic Imaging of Single Cancer Cells

Tu686 and H520 cells were grown to confluence in an 8-chamber glass slide. scFv-conjugated SERS tags at a concentration of 15 pM were introduced to 200 uL cell culture medium, and were then gently mixed for 30 min. After the incubation period, cells were washed thoroughly with PBS six times to remove free gold nanoparticles before imaging. The reflective mode darkfield images were obtained with an ExamineR microscope (DeltaNu, Laramie, Wyo.) using 20× objective. A dark field condenser was used to deliver a narrow beam of white light from a tungsten lamp to the sample. In this mode, cells stained with SERS nano-tags on the cell membrane displayed bright golden color due to the highly scattering property of gold nanoparticles. EGFR-negative H520 cells showed a mostly dark background. The Tu686 EGFR-positive cells exhibited a high level of EGFR receptor binding while the H520 EGFR-negative cells had only limited EGFR expression. Single-cell SERS spectra were obtained by switching the microscope to the Raman mode with 785 nm laser excitation. The laser spot size using 20× objective was 5×10 μm at the focal plane. FIG. 8 showed the SERS spectra recorded from the areas as indicated by the arrows for EGFR-positive and EGFR-negative cells, respectively. Each spectrum was acquired with an exposure time of 10 seconds.

Example 15

Biodistribution Studies of Nontargeted (Control) SERS Nanoparticles

Figure 9:
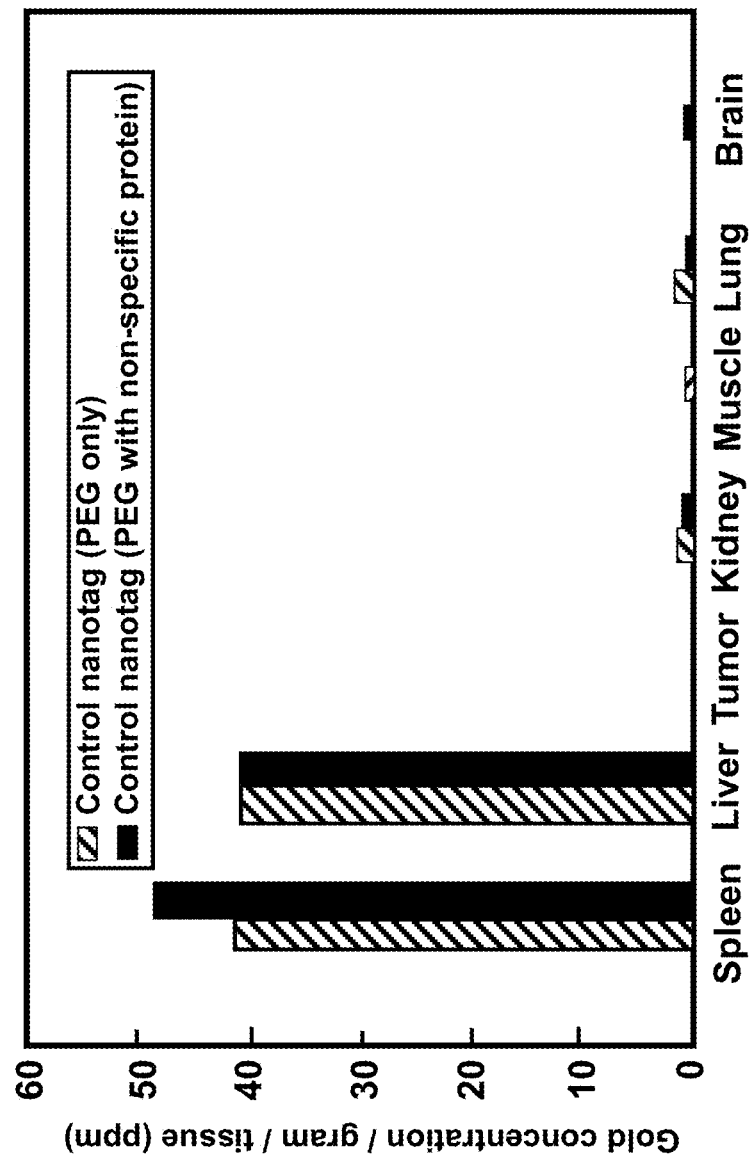
FIG. 9 illustrates a comparison of in-vivo distribution and tumor uptake data for plain PEG-coated nanoparticles and PEG-nanotags that are conjugated with a size-matched non-specific protein (27-KD recombinant GFP). The data were obtained at 5 hours post injection by inductively coupled plasma-mass spectrometric (ICP-MS) analysis of elemental gold.

To investigate the behavior of SERS nanostructure target-specific antibody conjugated probes in living animals, the following were examined: their specific uptake and retention, background or nonspecific uptake, blood clearance, and organ distribution. Nonspecific nanostructure uptake and retention took place primarily in the liver and the spleen, with little or no SERS nanostructure accumulation in the brain, the heart, the kidney, or the lung, as shown in FIG. 9. This pattern of in vivo organ uptake and distribution was similar to that of dextran-coated magnetic iron oxide nanoparticles. For polymer-encapsulated SERS nanoparticles with excess COOH groups, no tumor targeting was observed, indicating nonspecific organ uptake and rapid blood clearance. For polymer-encapsulated SERS nanoparticles with surface PEG groups, the rate of organ uptake was reduced and the length of blood circulation was improved, leading to slow accumulation of the nanoparticles in the tumors. For nanoparticles encapsulated by PEG and bioconjugated with an anti-EGFR antibody, the nanoparticles were delivered and retained by the tumor xenografts, but nonspecific liver and spleen uptake was still apparent, as shown in FIG. 6.

Example 16

Intracellular Localization Studies by Transmission Electron Microscopy (TEM)

Tumor, liver, spleen and kidney were examined with TEM to determine where the gold nanoparticles are deposited after cellular and tissue uptake. FIG. 10 shows a representative TEM image of tumor tissue sections when EGFR targeted gold nanoparticles were injected systemically for in-vivo tumor targeting. The data clearly show that the gold nanoparticles are internalized into tumor cells (most likely via receptor-mediated endocytosis) and are located in intracellular organelles such as endosomes and lysosomes.

To examine liver uptake of the nanoparticles, FIG. 11 shows a Kupffer cell (macrophages lining the liver sinudoidal surface) with gold nanoparticles captured in early- and late-stage endosomes. Note that the nanoparticles nonspecifically taken up by Kupffer cells are often isolated structures, in contrast to the clustered structures inside tumor cells. A significant number of gold nanoparticles are also identified inside spleen macrophage cells. In all other organs, gold particles are only found at very low densities. Overall, high-magnification TEM studies reveal that pegylated gold nanoparticles are taken up into intracellular organelles under in-vivo conditions, but their shape and morphology remain intact.

Example 17

Figure 12:
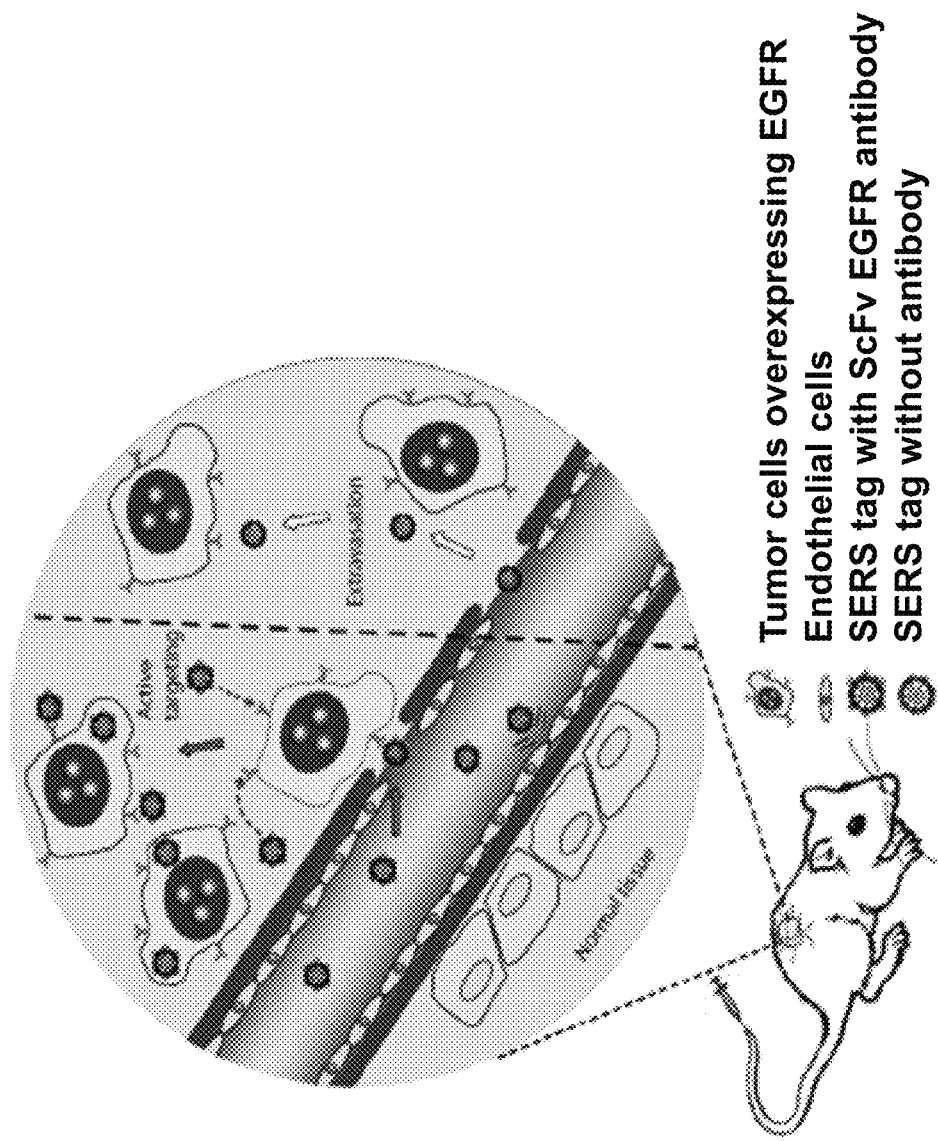
FIG. 12 shows a schematic diagram of pegylated SERS nanoparticles involved in active and passive tumor targeting. Both the control and targeted nanoparticles can accumulate in tumors through the EPR effect (enhanced permeability and retention effect), but only the targeted nanoparticles can recognize EGFR-positive cancer cells and rapidly enter these cells by receptor-mediated endocytosis.
Figure 13:
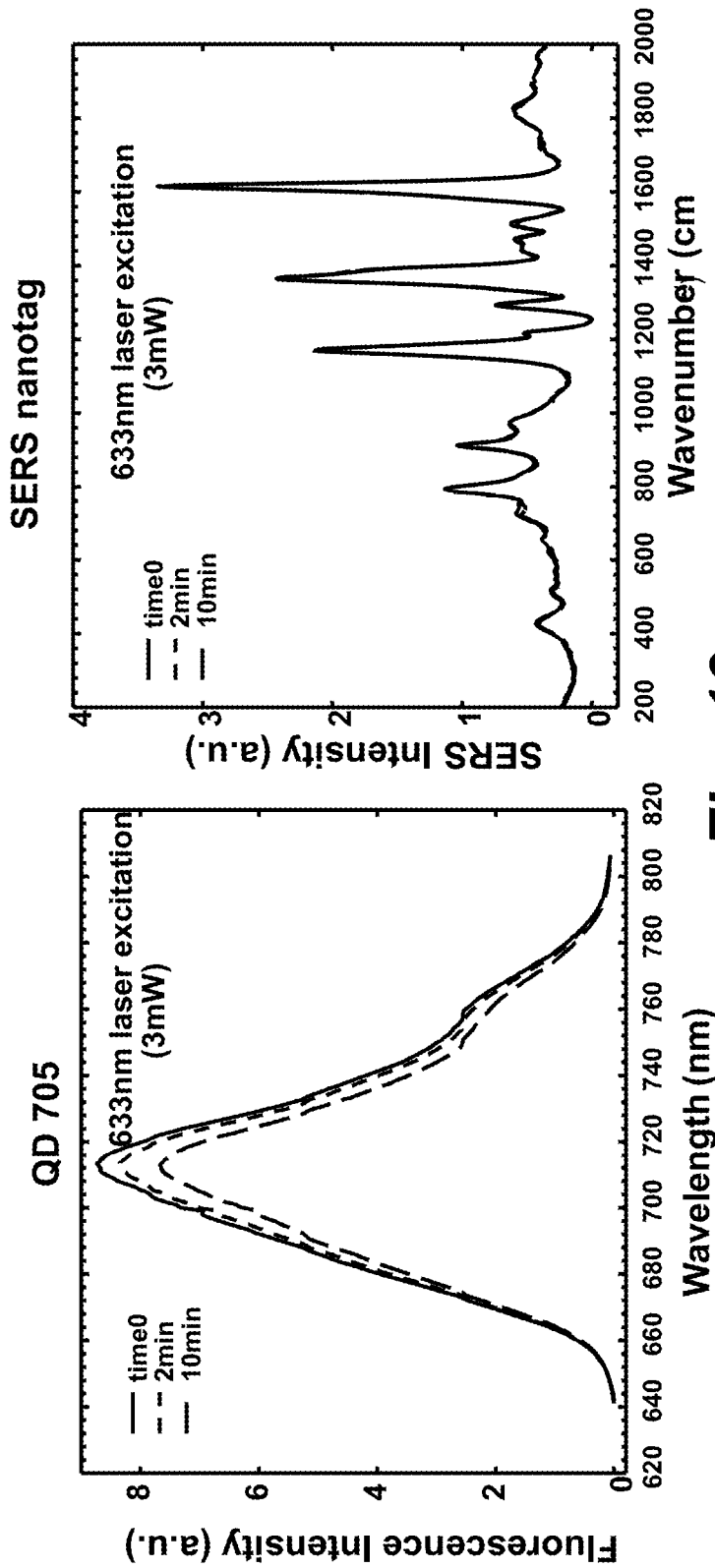
FIG. 13 compares the photostability of an SERS nanostructure of the disclosure and the quantum dot QD705.
Figure 14:
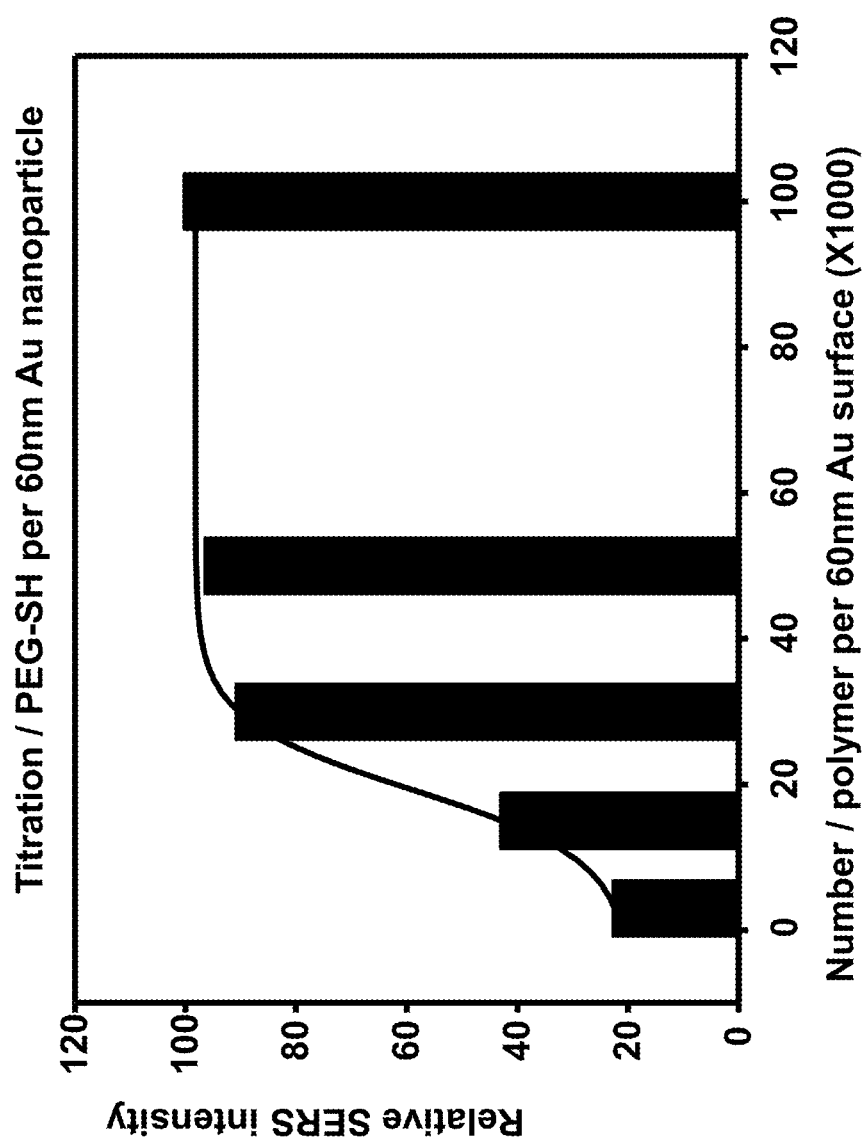
FIG. 14 illustrates the intensity of the SERS signal versus the number of thiol-polyethylene glycols attached to a 60 nm gold surface.
Figure 15:
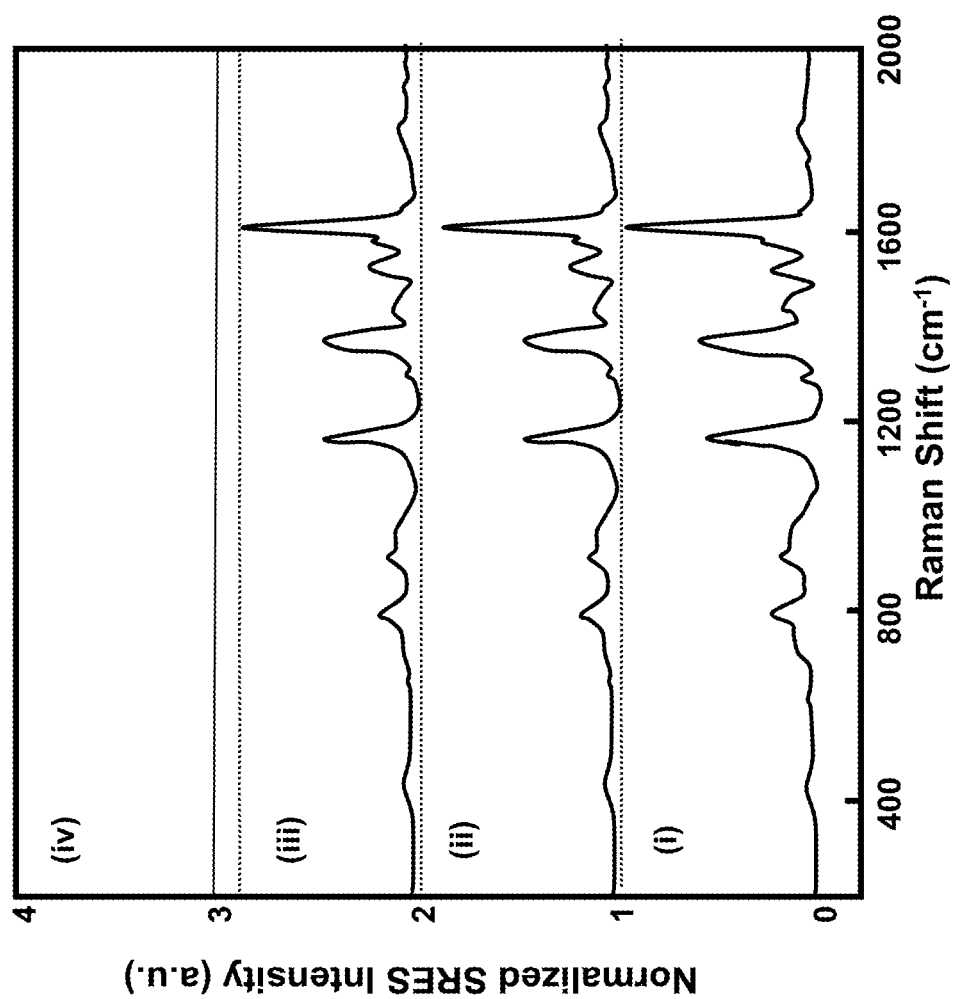
FIG. 15 illustrates the 'lock-out effect' of encapsulating the gold nanoparticle with a PEG-SH layer. (i) without PEG-SH coating; (ii) 30,000 PEG-SH per nanoparticle; (iii) 300,000 PEG-SH per nanoparticle; and (iv) PEG-SH attached before adding reporter-dye locked out from nanoparticle.
Figure 16:
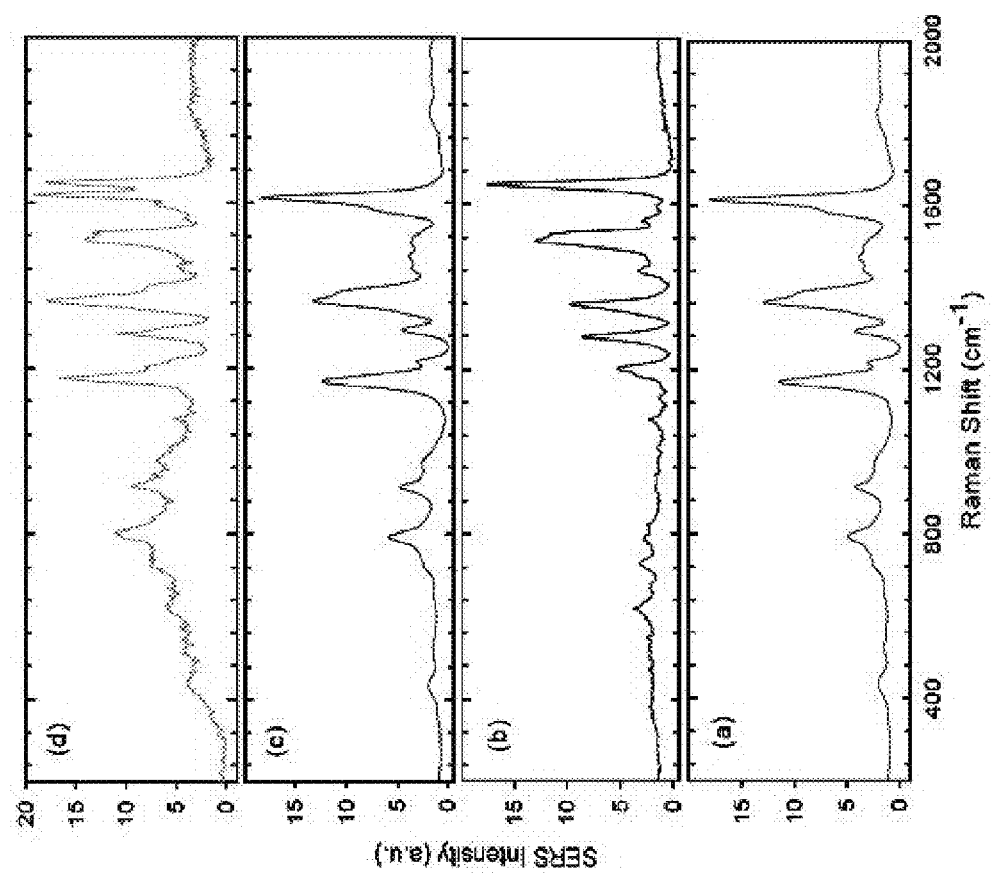
FIG. 16 illustrates that a PEG coating prevents cross-talk between a reporter molecule attached to the nanoparticle and a dye on the outer surface of the PEG layer. (a) Au-MGITC alone; (b) Au-RBITC alone; (c) RBITC locked out; and (d) 2 dyes co-absorbed on the nanoparticle.
Figure 17:
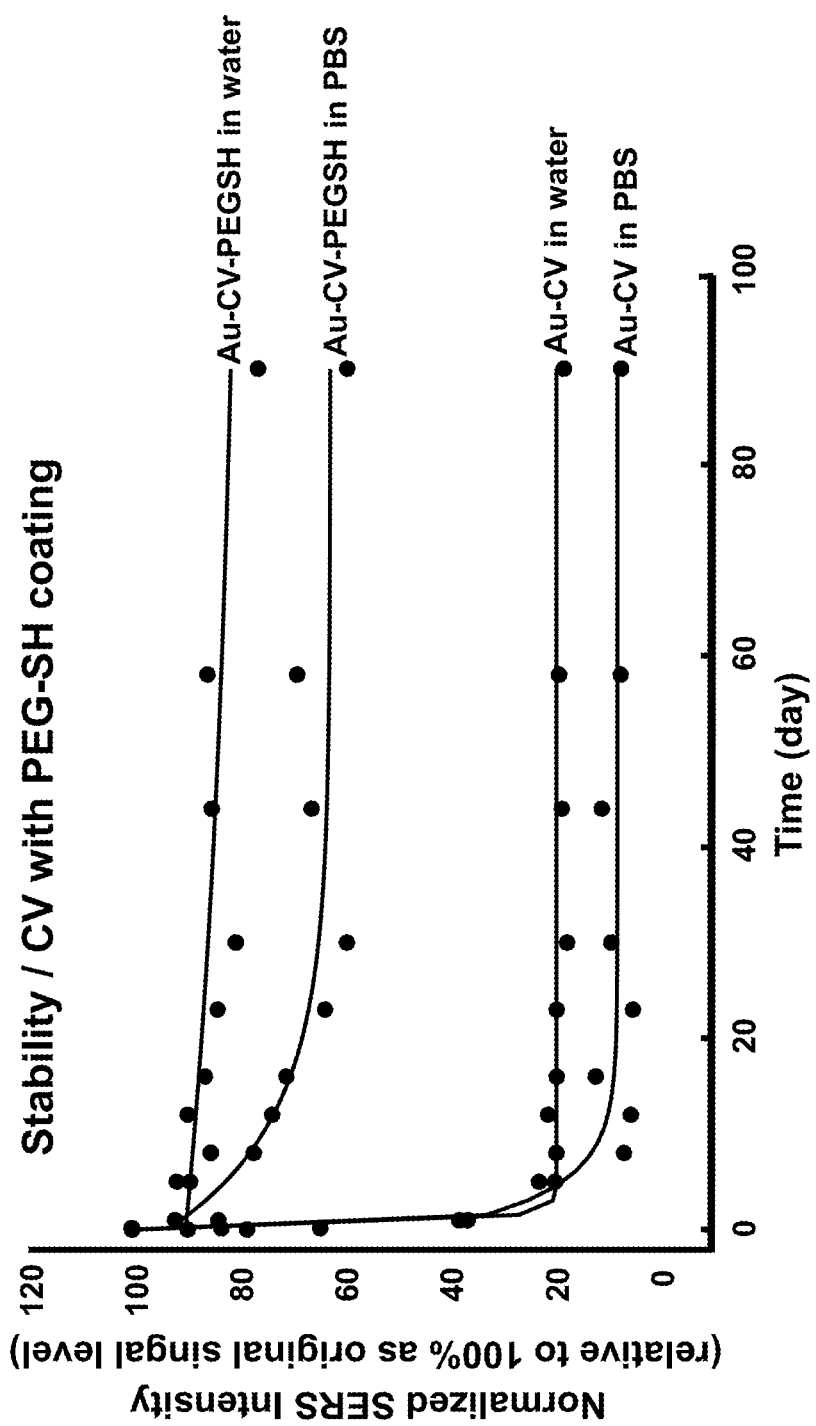
FIG. 17 illustrates the long-term stability of PEG coated particles.

Passive Accumulation Versus Active Targeting of SERS Nanoparticle Tags to Tumors See FIG. 12.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims

What we claim:

1. A surface-enhanced Raman spectroscopic active composite nanostructure comprising:
    a single-core metallic nanoparticle with a diameter of 100 nm or less;
    a Raman reporter molecule disposed on the surface of the core; and
    an encapsulating protective layer disposed on the surface of the core and the reporter molecule, wherein the encapsulating protective layer is a thiolpolyethylene glycol, and wherein the encapsulated reporter molecule has a measurable surface-enhanced Raman spectroscopic signature.

2. The nanostructure of claim 1, wherein the Raman reporter molecule is selected from an isothiocyanate dye, a multi-sulfur organic dye, a multi-heterosulfur organic dye, a benzotriazole dye, or combinations thereof.

3. The nanostructure of claim 1, wherein the reporter molecule is selected from a thiacyanine dye, a dithiacyanine dye, a thiacarbocyanine dye, or a dithiacarbocyanine dye.

4. The nanostructure of claim 1, wherein the reporter molecule is selected from malachite green isothiocyanate, tetramethylrhodamine-5-isothiocyante, X-rhodamine-5-isothiocyanate, X-rhodamine-6-isothiocyanate, or 3,3'-diethyl-thiadicarbocyanine iodide.

5. The nanostructure of claim 1, wherein the core metallic nanoparticle is gold.

6. The nanostructure of claim 1, further comprising a target-specific probe selectively binding a target on a cell.

7. The nanostructure of claim 6 wherein the target-specific probe is selected from the group consisting of an antibody, immunoglobulin, immunoglobulin fragment, a polypeptide, a polynucleotide, a drug molecule, an inhibitor compound, and a combination thereof, and wherein the targeting probe has an affinity for a marker on the surface of a target cell.

8. The nanostructure of claim 6, wherein the target-specific probe is disposed on the encapsulating protective layer.

9. The nanostructure of claim 6, wherein the target-specific probe is a tumor-targeting ligand.

10. A surface-enhanced Raman spectroscopic active composite nanostructure comprising:
    a single-core metallic nanoparticle with a diameter of 100 nm or less;
    a Raman reporter molecule without an isothiocyanate group disposed on the surface of the core; and
    an encapsulating protective layer disposed on the surface of the core and the reporter molecule, wherein the encapsulating protective layer is a thiolpolyethylene glycol, and wherein the encapsulated reporter molecule has a measurable surface-enhanced Raman spectroscopic signature.

11. The nanostructure of claim 10, wherein the Raman reporter molecule is selected from a multi-sulfur organic dye, a multi-heterosulfur organic dye, a benzotriazole dye, or combinations thereof.

12. The nanostructure of claim 10, wherein the reporter molecule is selected from a thiacyanine dye, a dithiacyanine dye, a thiacarbocyanine dye, or a dithiacarbocyanine dye.

13. The nanostructure of claim 10, wherein the reporter molecule is 3,3'-diethylthiadicarbocyanine iodide.

14. The nanostructure of claim 10, wherein the core metallic nanoparticle is gold.

15. The nanostructure of claim 10, further comprising a target-specific probe selectively binding a target on a cell.

16. The nanostructure of claim 15 wherein the target-specific probe is selected from the group consisting of an antibody, a polypeptide, a polynucleotide, a drug molecule, an inhibitor compound, and a combination thereof, and wherein the targeting probe has an affinity for a marker on the surface of a target cell.

17. The nanostructure of claim 15, wherein the target-specific probe is disposed on the encapsulating protective layer.

18. The nanostructure of claim 15, wherein the target-specific probe is a tumor-targeting ligand.

* * * * *